(12) United States Patent
Lee

(10) Patent No.: US 9,283,127 B2
(45) Date of Patent: Mar. 15, 2016

(54) ABSORBENT ARTICLES WITH DECOLORIZING STRUCTURES

(71) Applicant: Kimberly-Clark Worldwide, Inc., Neenah, WI (US)

(72) Inventor: SangWook Lee, Seongnam-si (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 227 days.

(21) Appl. No.: 13/851,932

(22) Filed: Mar. 27, 2013

(65) Prior Publication Data

US 2013/0261585 A1    Oct. 3, 2013

Related U.S. Application Data

(60) Provisional application No. 61/618,172, filed on Mar. 30, 2012, provisional application No. 61/695,481, filed on Aug. 31, 2012.

(51) Int. Cl.
| | |
|---|---|
| A61F 13/15 | (2006.01) |
| A61F 13/84 | (2006.01) |
| A61F 13/475 | (2006.01) |
| A61F 13/513 | (2006.01) |
| A61F 13/472 | (2006.01) |
| A61F 13/511 | (2006.01) |
| A61F 13/494 | (2006.01) |

(52) U.S. Cl.
CPC ......... *A61F 13/8405* (2013.01); *A61F 13/4755* (2013.01); *A61F 13/47263* (2013.01); *A61F 13/49446* (2013.01); *A61F 13/513* (2013.01); *A61F 13/5116* (2013.01); *A61F 13/51113* (2013.01); *A61F 2013/51178* (2013.01)

(58) Field of Classification Search
CPC . A61F 13/475; A61F 13/4755; A61F 13/494; A61F 13/4942; A61F 13/49446; A61F 13/5116; A61F 13/513; A61F 13/51394; A61F 2013/51165; A61F 2013/51377; A61F 2013/51378
See application file for complete search history.

(56) References Cited

U.S. PATENT DOCUMENTS

| | | | |
|---|---|---|---|
| 2,236,529 | A | 4/1941 | Epstein et al. |
| 2,418,907 | A | 4/1947 | Schreiber |
| 2,542,909 | A | 2/1951 | De Wet et al. |
| 3,124,135 | A | 3/1964 | Olson |
| 3,287,222 | A | 11/1966 | Raymond et al. |
| 3,338,992 | A | 8/1967 | Kinney |

(Continued)

FOREIGN PATENT DOCUMENTS

| | | |
|---|---|---|
| CN | 1034932 A | 8/1989 |
| CN | 1616115 A | 5/2005 |

(Continued)

OTHER PUBLICATIONS

Co-pending U.S. Appl. No. 13/851,927, filed Mar. 27, 2013, by Lee et al. for "Absorbent Articles with Decolorizing Agents."

(Continued)

*Primary Examiner* — Lynne Anderson
(74) *Attorney, Agent, or Firm* — Steven D. Flack

(57) ABSTRACT

A feminine hygiene absorbent personal care article includes a topsheet layer, a backsheet layer, at least one absorbent core layer positioned between the topsheet layer and the backsheet layer and a decolorizing structure positioned along the article side edges, with the decolorizing structure extending laterally beyond the lateral most side edges of the absorbent core layer.

12 Claims, 8 Drawing Sheets

(56) References Cited

U.S. PATENT DOCUMENTS

| | | |
|---|---|---|
| 3,341,394 A | 9/1967 | Kinney |
| 3,347,236 A | 10/1967 | David |
| 3,397,697 A | 8/1968 | Rickard |
| 3,398,097 A | 8/1968 | Kersnar et al. |
| 3,490,454 A | 1/1970 | Goldfarb et al. |
| 3,502,538 A | 3/1970 | Petersen |
| 3,502,763 A | 3/1970 | Hartmann |
| 3,542,615 A | 11/1970 | Dobo et al. |
| 3,635,828 A | 1/1972 | Benjamin et al. |
| 3,663,445 A | 5/1972 | Augustin et al. |
| 3,692,618 A | 9/1972 | Dorschner et al. |
| 3,783,872 A | 1/1974 | King |
| 3,802,817 A | 4/1974 | Matsuki et al. |
| 3,814,101 A | 6/1974 | Kozak |
| 3,849,241 A | 11/1974 | Butin et al. |
| 3,953,351 A | 4/1976 | Keller |
| 3,979,318 A | 9/1976 | Tokiwa et al. |
| 4,100,324 A | 7/1978 | Anderson et al. |
| 4,190,563 A | 2/1980 | Bosley et al. |
| 4,250,257 A | 2/1981 | Lee et al. |
| 4,259,383 A | 3/1981 | Eggensperger et al. |
| 4,288,225 A | 9/1981 | Roland et al. |
| 4,340,563 A | 7/1982 | Appel et al. |
| 4,357,939 A | 11/1982 | Jackson et al. |
| 4,363,322 A | 12/1982 | Andersson |
| 4,381,784 A | 5/1983 | Aberson et al. |
| 4,431,560 A | 2/1984 | Lake et al. |
| 4,532,232 A | 7/1985 | Larsson et al. |
| 4,585,650 A | 4/1986 | Newberry, Jr. et al. |
| 4,594,327 A | 6/1986 | Zuk |
| 4,636,209 A | 1/1987 | Lassen |
| 4,655,759 A | 4/1987 | Romans-Hess et al. |
| 4,673,524 A | 6/1987 | Dean |
| 4,693,713 A | 9/1987 | Chmelir et al. |
| 4,773,423 A | 9/1988 | Hakky |
| 4,798,603 A | 1/1989 | Meyer et al. |
| 4,801,494 A | 1/1989 | Datta et al. |
| 4,803,153 A | 2/1989 | Shibata et al. |
| 4,847,089 A | 7/1989 | Kramer et al. |
| 4,855,108 A | 8/1989 | Masuda et al. |
| 4,886,512 A | 12/1989 | Damico et al. |
| 4,892,534 A | 1/1990 | Datta et al. |
| 4,908,026 A | 3/1990 | Becker et al. |
| 4,933,092 A | 6/1990 | Aunet et al. |
| 5,009,716 A | 4/1991 | Gerson |
| 5,037,412 A | 8/1991 | Tanzer et al. |
| 5,064,541 A | 11/1991 | Jeng et al. |
| 5,118,428 A | 6/1992 | Sand et al. |
| 5,147,698 A | 9/1992 | Cole |
| 5,223,284 A | 6/1993 | Kulczycki, Jr. et al. |
| 5,248,309 A | 9/1993 | Serbiak et al. |
| 5,262,153 A | 11/1993 | Mishima et al. |
| 5,281,208 A | 1/1994 | Thompson et al. |
| 5,284,703 A | 2/1994 | Everhart et al. |
| 5,340,493 A | 8/1994 | Principato |
| 5,340,495 A | 8/1994 | Mulcahy et al. |
| 5,350,624 A | 9/1994 | Georger et al. |
| 5,382,400 A | 1/1995 | Pike et al. |
| 5,389,282 A | 2/1995 | Saijo et al. |
| 5,401,267 A | 3/1995 | Couture-Dorschner et al. |
| 5,407,442 A | 4/1995 | Karapasha |
| 5,415,640 A | 5/1995 | Kirby et al. |
| 5,434,059 A | 7/1995 | Balaraman et al. |
| 5,447,689 A | 9/1995 | Gibboni et al. |
| 5,505,720 A | 4/1996 | Hujber et al. |
| 5,527,892 A | 6/1996 | Borsotti et al. |
| 5,558,659 A | 9/1996 | Sherrod et al. |
| 5,558,834 A | 9/1996 | Chu et al. |
| 5,575,785 A | 11/1996 | Gryskiewicz et al. |
| 5,595,754 A | 1/1997 | Ito et al. |
| 5,607,414 A | 3/1997 | Richards et al. |
| 5,607,760 A | 3/1997 | Roe |
| 5,614,295 A | 3/1997 | Quincy, III et al. |
| 5,649,916 A | 7/1997 | Dipalma et al. |
| 5,652,148 A | 7/1997 | Doshi et al. |
| 5,660,798 A | 8/1997 | Doshi et al. |
| 5,695,679 A | 12/1997 | Christie et al. |
| 5,755,710 A * | 5/1998 | Menard .................. 604/378 |
| 5,762,642 A | 6/1998 | Coles et al. |
| 5,766,552 A | 6/1998 | Doshi et al. |
| 5,770,543 A | 6/1998 | Garst et al. |
| 5,785,696 A | 7/1998 | Inoue et al. |
| 5,795,344 A | 8/1998 | Chappell |
| 5,807,361 A | 9/1998 | Kajikawa et al. |
| 5,810,798 A | 9/1998 | Finch et al. |
| 5,883,231 A | 3/1999 | Achter et al. |
| 5,899,893 A | 5/1999 | Dyer et al. |
| 5,912,194 A | 6/1999 | Everhart et al. |
| 5,961,505 A | 10/1999 | Coe et al. |
| 6,110,158 A | 8/2000 | Kielpikowski |
| 6,117,523 A * | 9/2000 | Sugahara .................. 428/134 |
| 6,168,654 B1 | 1/2001 | Nohr et al. |
| 6,171,682 B1 | 1/2001 | Raidel et al. |
| 6,172,276 B1 | 1/2001 | Hetzler et al. |
| 6,231,719 B1 | 5/2001 | Garvey et al. |
| 6,241,714 B1 | 6/2001 | Raidel et al. |
| 6,322,544 B1 | 11/2001 | Laughlin et al. |
| 6,348,253 B1 | 2/2002 | Daley et al. |
| 6,350,711 B1 | 2/2002 | Potts et al. |
| 6,369,293 B1 | 4/2002 | Reeves et al. |
| 6,436,080 B1 | 8/2002 | Carlucci et al. |
| 6,471,728 B2 | 10/2002 | Smith et al. |
| 6,511,465 B1 | 1/2003 | Freiburger et al. |
| 6,528,698 B2 | 3/2003 | Mizutani et al. |
| 6,534,149 B1 | 3/2003 | Daley et al. |
| 6,548,731 B2 | 4/2003 | Mizutani et al. |
| 6,559,353 B1 | 5/2003 | Sheridan |
| 6,580,015 B2 | 6/2003 | Reeves et al. |
| 6,586,653 B2 | 7/2003 | Graeme, III et al. |
| 6,613,028 B1 | 9/2003 | Daley et al. |
| 6,642,430 B1 | 11/2003 | Busam et al. |
| 6,663,611 B2 | 12/2003 | Blaney et al. |
| 6,667,424 B1 | 12/2003 | Hamilton et al. |
| 6,669,932 B2 | 12/2003 | Imanaka et al. |
| 6,673,374 B2 | 1/2004 | Murad |
| 6,673,982 B1 | 1/2004 | Chen et al. |
| 6,677,498 B2 | 1/2004 | Chen et al. |
| 6,696,240 B1 | 2/2004 | Kloepfer et al. |
| 6,703,538 B2 | 3/2004 | Lassen et al. |
| 6,730,819 B1 | 5/2004 | Pesce |
| 6,812,169 B2 | 11/2004 | Potts et al. |
| 6,838,423 B2 | 1/2005 | Irvin et al. |
| 6,867,344 B2 | 3/2005 | Potts et al. |
| 6,875,617 B2 | 4/2005 | Alam |
| 6,888,044 B2 | 5/2005 | Fell et al. |
| 6,896,669 B2 | 5/2005 | Krautkramer et al. |
| 6,929,629 B2 | 8/2005 | Drevik et al. |
| 6,932,929 B2 | 8/2005 | Krautkramer et al. |
| 6,974,891 B2 | 12/2005 | Wallstroem |
| 6,984,770 B2 | 1/2006 | Graeme, III et al. |
| 7,105,715 B2 | 9/2006 | Carlucci et al. |
| 7,160,278 B2 | 1/2007 | Mizutani et al. |
| 7,241,627 B2 | 7/2007 | Wilhelm et al. |
| D558,335 S | 12/2007 | Willhaus |
| 7,316,673 B2 | 1/2008 | Drevik et al. |
| 7,388,123 B2 | 6/2008 | Cowell et al. |
| 7,402,157 B2 | 7/2008 | Christon et al. |
| 7,429,689 B2 | 9/2008 | Chen et al. |
| 7,431,715 B2 | 10/2008 | Guidotti et al. |
| 7,431,775 B2 | 10/2008 | Wang et al. |
| 7,504,551 B2 | 3/2009 | Herfert et al. |
| 7,687,681 B2 | 3/2010 | Di et al. |
| 7,695,726 B2 | 4/2010 | Rosevear et al. |
| 7,722,906 B2 | 5/2010 | Kandil |
| 7,723,093 B2 | 5/2010 | Kwon et al. |
| 7,837,944 B2 | 11/2010 | Auner et al. |
| 7,846,281 B2 | 12/2010 | Muvundamina |
| 7,879,744 B2 | 2/2011 | Seidling et al. |
| 7,928,282 B2 | 4/2011 | Dibb et al. |
| 8,003,780 B2 | 8/2011 | Kim et al. |
| 8,029,487 B2 | 10/2011 | Bagger-Sjoebaeck et al. |
| 8,148,598 B2 | 4/2012 | Tsang et al. |
| 8,211,078 B2 | 7/2012 | Noel |
| 8,241,915 B2 | 8/2012 | Adamczyk et al. |

(56) References Cited

U.S. PATENT DOCUMENTS

| | | | |
|---|---|---|---|
| 8,283,515 B2 | 10/2012 | Lagerstedt-Eidrup et al. | |
| 8,367,013 B2 | 2/2013 | Kaylor et al. | |
| 8,461,411 B2 | 6/2013 | Digiacomantonio et al. | |
| 8,461,412 B2 | 6/2013 | Febo et al. | |
| 8,569,221 B2 | 10/2013 | Cunningham et al. | |
| 8,847,002 B2 | 9/2014 | Goh et al. | |
| 2002/0022813 A1 | 2/2002 | Bewick-Sonntag et al. | |
| 2002/0054918 A1 | 5/2002 | Murad | |
| 2002/0082571 A1 | 6/2002 | Krivan et al. | |
| 2002/0120242 A1 | 8/2002 | Tyrrell et al. | |
| 2003/0100877 A1 | 5/2003 | Erdman | |
| 2003/0103916 A1 | 6/2003 | Imanaka et al. | |
| 2003/0109839 A1* | 6/2003 | Costea et al. | 604/358 |
| 2003/0114811 A1 | 6/2003 | Christon et al. | |
| 2003/0114818 A1 | 6/2003 | Benecke et al. | |
| 2003/0119202 A1 | 6/2003 | Kaylor et al. | |
| 2003/0124336 A1 | 7/2003 | Keane et al. | |
| 2003/0130631 A1 | 7/2003 | Springer et al. | |
| 2003/0162681 A1 | 8/2003 | Hage et al. | |
| 2003/0204178 A1 | 10/2003 | Febo et al. | |
| 2003/0208173 A1 | 11/2003 | Lagerstedt-Eidrup et al. | |
| 2004/0015145 A1* | 1/2004 | Miura et al. | 604/367 |
| 2004/0022678 A1 | 2/2004 | Komagoe et al. | |
| 2004/0060112 A1 | 4/2004 | Fell et al. | |
| 2004/0064119 A1 | 4/2004 | Guidotti et al. | |
| 2004/0127883 A1 | 7/2004 | Cowell et al. | |
| 2005/0079637 A1 | 4/2005 | Wilhelm et al. | |
| 2005/0148488 A1 | 7/2005 | Jekel et al. | |
| 2005/0163730 A1 | 7/2005 | Rosevear et al. | |
| 2005/0214241 A1 | 9/2005 | Kandil | |
| 2005/0256022 A1 | 11/2005 | May et al. | |
| 2006/0111266 A1 | 5/2006 | Abera et al. | |
| 2006/0127437 A1 | 6/2006 | Kennedy et al. | |
| 2006/0189817 A1 | 8/2006 | Horlacher et al. | |
| 2006/0198797 A1 | 9/2006 | Giniger | |
| 2006/0222675 A1 | 10/2006 | Sabnis et al. | |
| 2007/0027049 A1 | 2/2007 | Rigg | |
| 2007/0055210 A1 | 3/2007 | Kao | |
| 2007/0087954 A1 | 4/2007 | Wang et al. | |
| 2007/0093770 A1 | 4/2007 | Ecker et al. | |
| 2007/0116748 A1 | 5/2007 | Isele et al. | |
| 2007/0122360 A1 | 5/2007 | Oniki et al. | |
| 2007/0197987 A1 | 8/2007 | Tsang et al. | |
| 2008/0276379 A1 | 11/2008 | MacDonald et al. | |
| 2008/0277621 A1 | 11/2008 | MacDonald et al. | |
| 2008/0299609 A1 | 12/2008 | Kwon et al. | |
| 2009/0036856 A1 | 2/2009 | Woltman et al. | |
| 2009/0047363 A1 | 2/2009 | Itoi et al. | |
| 2009/0061718 A1 | 3/2009 | Seidling et al. | |
| 2009/0062172 A1 | 3/2009 | Cunningham et al. | |
| 2009/0062764 A1 | 3/2009 | MacDonald et al. | |
| 2009/0105676 A1 | 4/2009 | Brusk et al. | |
| 2009/0156536 A1 | 6/2009 | Kim et al. | |
| 2009/0157021 A1 | 6/2009 | Sullivan et al. | |
| 2009/0238847 A1 | 9/2009 | Itoi et al. | |
| 2009/0280553 A1 | 11/2009 | Mikami et al. | |
| 2009/0306615 A1* | 12/2009 | Olsson | 604/367 |
| 2010/0028638 A1 | 2/2010 | Reichardt et al. | |
| 2011/0004174 A1 | 1/2011 | Carlucci et al. | |
| 2011/0251575 A1 | 10/2011 | Kuroda et al. | |
| 2011/0288514 A1 | 11/2011 | Kuroda et al. | |
| 2012/0109088 A1* | 5/2012 | Komatsu et al. | 604/361 |
| 2012/0115718 A1 | 5/2012 | Nakashita et al. | |
| 2012/0141975 A1 | 6/2012 | Sato et al. | |
| 2012/0165773 A1 | 6/2012 | Nakashita et al. | |
| 2012/0215192 A1 | 8/2012 | Corbellini et al. | |
| 2012/0296303 A1 | 11/2012 | Ng et al. | |
| 2013/0012900 A1 | 1/2013 | Uda et al. | |
| 2013/0158494 A1 | 6/2013 | Ong et al. | |
| 2013/0261584 A1 | 10/2013 | Lee et al. | |
| 2013/0261585 A1 | 10/2013 | Lee | |
| 2013/0261586 A1 | 10/2013 | Lee et al. | |

FOREIGN PATENT DOCUMENTS

| | | |
|---|---|---|
| CN | 200948202 Y | 9/2007 |
| DE | 10 2009 029 194 A1 | 4/2011 |
| EP | 0 019 371 A1 | 11/1980 |
| EP | 0 355 842 A2 | 2/1990 |
| EP | 0 470 275 A1 | 2/1992 |
| EP | 0 560 630 B1 | 11/1998 |
| EP | 1 034 799 A1 | 9/2000 |
| EP | 1 034 801 A1 | 9/2000 |
| EP | 1 034 803 A1 | 9/2000 |
| EP | 1 034 804 A1 | 9/2000 |
| EP | 1 358 894 A1 | 11/2003 |
| EP | 1 295 711 B1 | 4/2006 |
| EP | 1 356 797 B1 | 12/2006 |
| EP | 1 159 014 B1 | 4/2007 |
| EP | 1 842 513 A1 | 10/2007 |
| EP | 2 269 661 B1 | 11/2012 |
| GB | 792531 A | 3/1958 |
| GB | 1 349 955 A | 4/1974 |
| GB | 2 090 137 A | 7/1982 |
| GB | 2 390 853 A | 1/2004 |
| JP | 63-134050 A | 6/1988 |
| JP | 01-186809 A | 7/1989 |
| JP | 01-213231 A | 8/1989 |
| JP | 03-172400 A | 7/1991 |
| JP | 03-215267 A | 9/1991 |
| JP | 7028890 B | 4/1995 |
| JP | 2001-070339 A | 3/2001 |
| JP | 4184253 B2 | 11/2008 |
| KR | 10-2009-0100645 A | 9/2009 |
| WO | WO 97/46219 A1 | 12/1997 |
| WO | WO 98/10928 A1 | 3/1998 |
| WO | WO 99/26588 A2 | 6/1999 |
| WO | WO 00/37039 A1 | 6/2000 |
| WO | WO 00/51655 A1 | 9/2000 |
| WO | WO 00/51656 A1 | 9/2000 |
| WO | WO 01/12241 A1 | 2/2001 |
| WO | WO 01/16268 A1 | 3/2001 |
| WO | WO 03/041752 A1 | 5/2003 |
| WO | WO 03/052390 A1 | 6/2003 |
| WO | WO 2005/107670 A2 | 11/2005 |
| WO | WO 2006/062679 A2 | 6/2006 |
| WO | WO 2006/117055 A1 | 11/2006 |
| WO | WO 2007/085626 A1 | 8/2007 |
| WO | WO 2008/139340 A1 | 11/2008 |
| WO | WO 2008/139341 A2 | 11/2008 |
| WO | WO 2009/027856 A2 | 3/2009 |
| WO | WO 2009/062998 A1 | 5/2009 |
| WO | WO 2009/133518 A2 | 11/2009 |
| WO | WO 2010/017158 A1 | 2/2010 |
| WO | WO 2011/027295 A2 | 3/2011 |
| WO | WO 2012/074512 A1 | 6/2012 |

OTHER PUBLICATIONS

Co-pending U.S. Appl. No. 13/851,941, filed Mar. 27, 2013, by Lee et al. for "Absorbent Articles with Improved Stain Decolorization."

American Society for Testing Materials (ASTM) Designation: E1164-02, "Standard Practice for Obtaining Spectrometric Data for Object-Color Evaluation," pp. 1-8, published Aug. 2002.

Cost, Frank, "Pocket Guide to Digital Printing," Delmar Publishers, Albany, NY, ISBN 0-8273-7592-1, pp. 144-145.

Field Guide to Stains—How to Identify and Remove Virtually Every Stain Known to Man, Quirk Productions, Inc., 2002, pp. 199-202.

Japanese Industrial Standard, JIS Z 8722:2000, "Methods of Colour Measurement—Reflecting and Transmitting Objects," 2000, 1-57 and 1 correction page, "Errata.".

Lindon, Jack et al., "A Biological Menses Simulant Using a 'Batch' Homogenization Process With Varying Levels of Rheological Properties," ip.com, IPCOM000198395D, Aug. 6, 2010, pp. 1-13.

Fatty acid. Wikipedia, Internet web page "http://en.wikipedia.org/wiki/Fatty_acid", viewed and printed Jul. 25, 2013, pp. 1-14.

Oxidizing agent. Wikipedia, Internet web page "http://en.wikipedia.org/wiki/Oxidizer", viewed and printed Jul. 25, 2013, pp. 1-6.

On-the-spot cleanup, Consumer Reports, Jun. 1998, p. 10.

(56) References Cited

OTHER PUBLICATIONS

Seeing Spots? Don't Rely on Quick Stain Removers, Consumer Reports, Aug. 2006, p. 9.
Stain Removers: Which Are Best?, Consumer Reports, Mar. 2000, p. 52.
Cacace, M.G. et al., "The Hoffmeister Series: Salt and Solvent Effects on Interfacial Phenomena," Quarterly Reviews of Biophysics, vol. 30, No. 3, 1997, pp. 241-277.
Senczuk, Anna M. et al., "Hydrophobic Interaction Chromatography in Dual Salt System Increases Protein Binding Capacity," Biotechnology and Bioengineering, vol. 103, No. 5, Aug. 1, 2009, pp. 930-935.

* cited by examiner and from U.S. Provisional Application No. 61/695,481
ABSORBENT ARTICLES WITH DECOLORIZING STRUCTURES This application claims the benefit of priority from U.S. Provisional Application No. 61/618,172 filed on Mar. 30, 2012 and from U.S. Provisional Application No. 61/695,481 filed on Aug. 31, 2012, the subject matter of each of which is hereby incorporated by reference herein in its entirety.

FIELD OF THE INVENTION

The present invention is generally directed to absorbent personal care articles. In particular, the present invention is directed to feminine hygiene absorbent personal care articles having layer structures which come in contact with menses exudates, and which structures can be used to physically separate such exudates.

BACKGROUND OF THE INVENTION

Feminine hygiene absorbent personal care articles are often used to collect and retain body fluids, liquids or exudates containing menses or blood. In the context of such products, comfort, absorbency, and discretion are three main product attributes and areas of concern for the wearer. In particular, wearers are often interested in knowing that such products will absorb significant volumes of menses exudates in order to protect their undergarments, outergarments, or bedsheets from staining, and that such products will help them avoid the subsequent embarrassment brought on by such staining. Wearers are also interested in using products that cannot be seen or felt through their undergarments.

Feminine hygiene absorbent personal care articles, such as sanitary napkins, pads and pantiliners, typically include at least one or more absorbent layers enclosed between a body-facing, liquid permeable topsheet layer and a garment-facing liquid impermeable backsheet layer. The absorbent layers and/or the topsheet and backsheet layers are often bonded together at their peripheral edges to form a seal around the article. In use, such articles are typically positioned in the crotch portion of an undergarment for absorption of bodily exudates, and are held in place via adhesive strips positioned on the undersurface of the articles (facing the garment). Some of these articles also include wing-like or flap structures for wrapping about the user's undergarments to further secure them to a user's underwear. Such wing-like structures are frequently made from lateral extensions of the topsheet and backsheet layers.

For many women, it is entirely routine to periodically view their hygienic articles during use, so as to monitor the appearance and spread of a menses insult (so as to avoid leakage throughout the day). For some women, a concern or cause of emotional discomfort with conventional feminine hygiene absorbent personal care articles is the expanding appearance of a menses insult in the article, and specifically, the spread of the menses stain to the side edges of a product. While many women often do not mind seeing a targeted staining in the center of a pad, and then change the pad accordingly, some women prefer not to see an extensive stain, other than the centralized insult stain. In contrast, some women prefer to see an expanding stain, as this provides indication of their level of flow that day, as well as evidence that the pad is collecting such exudates. Therefore stains on a feminine care pad can have a profound influence on the consumer use experience of the pad product. Stain size and intensity can influence perceptions of cleanliness and dryness as well as the performance of a pad. Obviously, the leakage of fluids when using such articles, particularly from around the side edges of the articles, is universally a cause of emotional concern. Such leakage may occur in the narrower product dimension along the longitudinally directed side edges, or along the lateral wing or flap areas. Product leakage may lead not only to embarrassment for the consumer, but also to a general loss of confidence in use of the articles. A very vivid menses stain positioned close to the edges on a pad may convey an impression that the pad is about to leak, which therefore impacts the consumer's perception of the pad's ability to deliver a sense of security against leakage.

Various attempts have therefore been made to incorporate structures into feminine hygienic pads to separate staining, direct staining, target staining, mask staining or discolor menses staining; to make more efficient use of as much of an absorbent product as possible; and to reduce or prevent leakage. Such structures include embossed walls or channels, shaped target areas such as openings from a top surface to a lower absorbent layer, polymeric or other liquid impermeable barrier walls, and the like. However, such attempts have not been completely successful at eliminating or addressing the leakage problem, or reducing consumer concerns over the severity of staining, if it actually were to occur.

Numerous absorbent structures have also been developed for capturing and retaining voluminous menses exudates released by women during their monthly cycles. In this regard, the designs of such absorbent pads and pantiliners have been refined over time, so as to make their usage more comfortable (physically and emotionally) to consumers. For example, originally when first developed, catamenial pads were thick and bulky structures, typically using cellulosic wadding as their sole or primary absorbent layer, such as described in U.S. Pat. No. 3,124,135 to Olson. Such pads were often readily visible through a wearer's outergarments, were used in conjunction with separate belts or tabs, and proved uncomfortable for a user to wear. These older "tabbed" or belted pads distributed menses predominantly in the depth direction/axis (also known as Z-axis) of the pad, and predominantly leaked through the back of the pad. This fluid distribution was driven by a close to the body fit, due to the pad use with belt construction. These pads were typically over ¾ inch thick (approximately 19.05 mm), and employed no impervious layers to impede menses or air movement through the pad, and offered no specific distribution materials to drive lateral or longitudinal fluid distribution. These older pads needed constructions that prevented downward distribution of the red stain of menses. Because these older pads leaked through the backsheet layer, constructions were of interest which minimized the staining (or stain size) on the backsheet layer. In contrast, modern pads seek to minimize staining on the topsheet layer (from which leakage may occur as a result of such pads being fastened to the undergarment, with less close-to-body fit). Further, the older pads also did not contain any superabsorbent that might interfere with the distribution of menses within the pad. As a result, such older constructions would not work adequately on modern, garment-attached pad arrangements.

As absorbent technology advanced, superabsorbent polymer chemistry and substrate layering designs have been developed, enabling manufacturers to produce feminine absorbent products with progressively thinner configurations. As a result, feminine hygiene sanitary napkins, pads and liners have become significantly thinner and more absorbent, so as to impart both comfort and a certain inconspicuousness to a wearer. For the most part, such thinner products have provided the users and surrounding third parties, with the impression that the user is not wearing any form of menses protection in her undergarments. Such articles have employed garment attachment systems.

The modern garment-attached pads predominantly distribute menses laterally and longitudinally, and predominantly leak, when they leak, off the side edges (longitudinally directed sides, front, and back edges) rather than through the pad bottom. This leakage distribution is driven by not-so-close pad body fit, due to attachment to underwear or panties, and the pad construction. These pads are typically less than ¼ inch thick (approximately 6.35 mm), have an impervious backsheet layer to impede menses and air movement through the pad, and utilize specific distribution materials to drive lateral and longitudinal distribution. Modern pads also contain superabsorbent that can interfere with the distribution of menses within the pad. The use of superabsorbent materials in core layers can lead to gel blocking that interferes with maximized fluid absorption.

Even with these advancements in absorbency, consumers continue to experience some leakage, typically from fluid run-off from the topsheet surface. Attempts have been put forth which use combinations of specific chemistry and substrates to filter blood from menses on feminine care article. For example, filtering using a "depth filter" is described in U.S. Pat. No. 6,350,711 to Potts et al. Still another reference which describes the use of specific salts to remove colored substances from aqueous fluids is U.S. patent publication 2012/0215192 to Corbellini et al.

Menses run-off from the topsheet of thin products is often the result of various "structural" and "action-based" root causes, which cause soiling of user garments or bedding. For example, structural causes may include impeded absorbency pathways, or inability to handle fluid surges. Action-based causes may be for example, consumers experiencing leakage from improper placement of such products in their undergarments, a consumer's use of such products beyond the product's designed lifespan, consumers choosing to wear an absorbent article that is ill equipped to handle their current menses flow rate, or further still, consumer movements during their daily activities which cause menses exudates to leak off of the absorbent article. Therefore, despite the development of many different absorbent technologies and structural designs, product leakage and the resulting stains caused from such leakage continue to concern potential users of such products. A need therefore exists for pad constructions that prevent lateral and longitudinal distribution of the red stain of menses. There is a further need for absorbent structures which utilize layering structures to reduce the severity/appearance of menses staining of both a user's pad, and a user's garments or bedding. There is also a need for absorbent articles which reduce a consumer's concern over any stain that might occur, as well as articles which more efficiently use absorbent systems to take up retained liquids.

SUMMARY OF THE INVENTION

A feminine hygiene absorbent personal care article having lateral side edges includes a topsheet layer, a backsheet layer, an optional additional interior layer, and at least one absorbent core layer having lateral side edges. The absorbent core layer is positioned between the topsheet layer and the backsheet layer. The feminine hygiene absorbent personal care article has a longitudinal axis, a transverse axis, and a depth axis, and at least one decolorizing structure is positioned on at least one of the topsheet layer, absorbent core layer, backsheet layer, optional additional interior layer or between one or more of the above layers within the feminine hygiene absorbent personal care article. The decolorizing structure is either along, adjacent, or at least partially adjacent the article side edges, such as in one embodiment between about 2 and 5 cm from the side edge, and extends laterally beyond the lateral most side edge(s) of the absorbent core layer (especially when viewed along the D axis).

In an alternative embodiment of the invention, the decolorizing structure is positioned on the topsheet layer. In a further alternative embodiment, the topsheet layer includes a central longitudinally directed topsheet material and two longitudinally directed side edge topsheet materials (or topsheet side cover layers), and the decolorizing structure is positioned on each of the two longitudinally directed side edge topsheet materials. In still a further alternative embodiment of the invention, the two longitudinally directed side edge topsheet materials are comprised of a laminate including a masking layer, which serves as a masking element. In yet a further alternative embodiment of the invention, the laminate side edge topsheet materials include a nonwoven and film layer. In still a further alternative embodiment, the decolorizing structures are present in a pair symmetrically located about the longitudinal axis (central). In still a further alternative embodiment, the decolorizing structures are in at least a separate plane than the absorbent core layers along the depth axis of the article.

In still a further alternative embodiment of the invention, the decolorizing structure is a laminate itself, of two nonwoven materials, In one embodiment of the invention two nonwoven materials in a laminate making up the decolorizing structure comprise a first nonwoven material having an average pore size of between about 50 and 200 microns, and a second nonwoven material having an average pore size of between about 3 and 40 microns. In yet a further embodiment of the invention the two nonwoven materials making up a laminated decolorizing structure demonstrate between a first nonwoven material and a second nonwoven material, an average pore size ratio of between 1:1 to 1:0.01 between the first nonwoven material and the second nonwoven material.

In still another alternative embodiment of the invention, decolorizing structures in the form of laminates are placed on or adjacent each longitudinally directed side edge of the article. In yet another alternative embodiment of the invention, the laminates making up the decolorizing structures have a length of between about 30 and 99 percent of the total length of the absorbent article.

In yet a further alternative embodiment of the invention, a feminine hygiene absorbent personal care article includes at least two decolorizing structures. In still a further alternative embodiment of the invention, at least two decolorizing structures are present in an article in or on at least two separate layers within the article. In still a further alternative embodiment of the invention, the decolorizing structures are projections off of a layer within the article. In still a further alternative embodiment of the invention, the decolorizing structures are extensions off of a layer within the article. In still a further alternative embodiment of the invention, additional decolorizing structures are placed on the front and back ends of the article. In yet a further alternative embodiment of the invention, the decolorizing structure is a film and nonwoven laminate. In still a further alternative embodiment of the invention, a decolorizing structure is a folded film and nonwoven laminate, such as a "U" shaped folded laminate, an "S" shaped folded laminate or an "M" shaped folded laminate. In still a further alternative embodiment, the laminate includes a colorant. In still another alternative embodiment, the decolorizing structure is positioned between the topsheet layer and an absorbent core layer. In still a further alternative embodiment, two decolorizing structures are placed in the feminine hygiene absorbent personal care article symmetrically across from one another along or adjacent the lateral side edges of the article, with a portion of the article located between them free of such decolorizing structures. Such portion of the article located between them is part of the central insult region/portion of the article.

In another alternative embodiment of the invention a feminine hygiene absorbent personal care article having lateral side edges, includes a topsheet layer, a backsheet layer, and at least one absorbent core layer having lateral side edges. The absorbent core layer is positioned between the topsheet layer and the backsheet layer. The feminine hygiene absorbent personal care article has a longitudinal axis, a transverse axis, and a depth axis, wherein at least one decolorizing structure is positioned on at least one of the topsheet layer, an absorbent core layer or backsheet layer within the feminine hygiene absorbent article, adjacent (or partially adjacent, or along) the article side edges, which decolorizing structure extends laterally beyond the lateral side edges of the absorbent core layer along the transverse axis. Such decolorizing structure(s) are desirably in different planes along the depth axis than the absorbent core layer(s). Such decolorizing structures are desirably in different planes along the depth axis than the topsheet layer. The decolorizing structure desirably includes a laminate of a first nonwoven material and a second material, being either a second nonwoven material, film material layer, or a combination thereof, with the first nonwoven material being either a meltblown or spunbond material and the second material being either a meltblown material, film material, or film and nonwoven laminate.

In still another alternative embodiment of the invention, a feminine hygiene absorbent personal care article has lateral side edges, and includes a topsheet layer having a user-facing surface, a backsheet layer, and at least one absorbent core layer having lateral side edges. The core layer is positioned between the topsheet layer and the backsheet layer, wherein at least one decolorizing structure for filtering coloring components of menses is positioned on at least one of the topsheet layer, an absorbent core layer or backsheet layer within the feminine hygiene absorbent personal care article and adjacent the article lateral side edges. The decolorizing structure extends laterally beyond the lateral side edges of the absorbent core layer and filters color from menses as menses contacts or crosses the decolorizing structure towards the article lateral side edges. In an alternative embodiment, the decolorizing structure masks menses stain when viewed from the user facing surface of the topsheet layer.

In yet another alternative embodiment of the invention, the deodorizing structures are placed within an article such that a menses stain viewed from the topsheet surface of an article is smaller in at least one dimension (the length, width or both) as compared to the stain on an interiorly-situated article layer, such as an absorbent core layer.

Objects and advantages of the invention are set forth below in the following description, or may be learned through practice of the invention.

BRIEF DESCRIPTION OF THE DRAWINGS

A full and enabling disclosure of the present invention is set forth more particularly in the remainder of the specification, including reference to the accompanying figures, in which.

DETAILED DESCRIPTION OF PREFERRED EMBODIMENTS

Definitions

Figure 1:
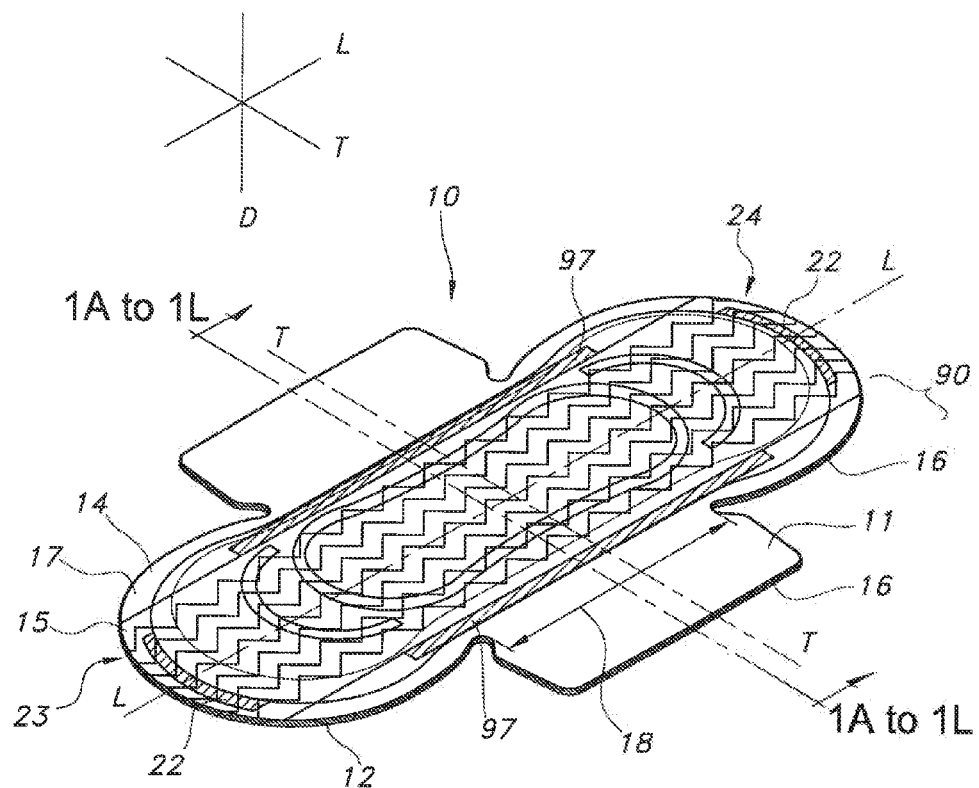
FIG. 1 is a top perspective view of an embodiment of the present invention in the form of a feminine hygienic pad.

As used herein the term "nonwoven fabric or web" refers to a web having a structure of individual fibers or threads which are interlaid, but not in an identifiable manner as in a knitted fabric. Nonwoven fabrics or webs have been formed from many processes such as for example, meltblowing processes, spunbonding processes, bonded carded web processes, etc. The basis weight of nonwoven webs may generally vary, such as from about 5 grams per square meter ("gsm") to 150 gsm, hi some embodiments from about 10 gsm to about 125 gsm, and in some embodiments, from about 25 gsm to about 120 gsm.

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki. et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

As used herein, the term "coform" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; each of which are incorporated herein in their entirety by reference thereto for all purposes.

As used herein, the term "masking element" shall refer to an actual physical structure which obscures or partially hides a view of a stain (when the article is viewed by a user from above the article topsheet layer), such as a material sheet or layer, which obscures the visualization/perception of a blood stain. Such a masking element is desirably a film and/or fibrous hydrophobic barrier material. Such a masking element, for the purposes of this invention, is desirably not absorbent, although it may be liquid permeable, such as allowing permeation through apertures. In one embodiment, it would be a nonabsorbent and liquid impermeable material.

As used herein, the term "decolorizing structure" shall refer to a layer structure or laminate which decolorizes blood stains by filtering blood cells or blood colorants from blood-containing fluids (such as menses), with the final effect being a decrease or elimination of the red color intensity in certain portions of a feminine hygiene absorbent personal care article and/or the fluid flowing out of a feminine hygiene absorbent personal care article. Such decolorizing structure effectively removes or alters the color of potentially staining fluid, so that fluid which unfortunately travels through or over/across such a structure in the absorbent article to the article side edges (and in particular lateral side edges), has less color for staining of garments or bedding, should there be an actual leak of fluid off of the article. By trapping menses coloring agents in particular or targeted article areas laterally outside of the absorbent layer(s), additional absorption of the menses non-colored fluids (lower viscosity clear fluids), may occur throughout dedicated absorbent core areas. Such decolorizing structures may also mask staining (when viewed from above the topsheet layer) by their layer structure and/or coloration.

For the purposes of this disclosure, decolorizing structures are desirably positioned on an article in symmetrical locations that are lateral to the central longitudinal axis of the absorbent article, and desirably extend laterally beyond the longitudinally directed lateral side edges of at least the main absorbent core layer(s) along the transverse axis (when viewed through cross-section in the depth direction or z-axis). Such laterally extending decolorizing structures, can project (as projections) upward or downward from a non-absorbent layer, or extend (as extensions) beyond the lateral core layer edge (that is projecting more laterally towards the article lateral side edge than the core layer(s)), or can be a combination of one or more of the foregoing. Such projections can project more laterally, from either a layer above the core or below the core (when viewed along the depth axis (direction) or z-axis), or alternatively extend laterally from an attachment or encasement material on the core layer itself. Essentially, while such decolorizing structures are desirably in planes different from the core layer(s) planes, along the D-axis, they may be in the same planes.

The decolorizing structure shall refer to a single layer material, a multiple-layered material structure, a laminate or laminae structure, or a combination thereof, but desirably is a laminate structure. Examples of laminate-type structures are described in U.S. Pat, Nos. 6,932,929 and 6,896,669 to Woltman, each of which are hereby incorporated by reference in its entirety. Such laminate type structures may include laminates of multiple nonwoven layers, or laminates of one or more nonwoven layers and a film layer. In such an instance, use of a film layer can serve as a masking element to help shield viewing of a stain from above the topsheet layer, especially by use of a pigment within the film. Such masking element may also assist in the directing of a stain to certain filtering elements of the decolorizing structure or to an absorbent core layer within the article. For example, if the decolorizing structure is in the shape of an "S" folded structure, use of a film layer beneath a nonwoven layer in the "S" folded configuration can direct insult flow in the curvilinear path of the "S" fold along the D-axis (depth direction), keeping it from spreading off the article side edges, as well as can block nondesired transfer of insult through certain portions of the pad structure. Such folded decolorizing structure configurations are desirably tacked down within the article to further prevent lateral flow of menses or stain to the article lateral edges.

As used herein, the terms "superabsorbent polymer," "superabsorbent" or "SAP" shall be used interchangeably and shall mean polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. A SAP's ability to absorb water is based in part on ionicity (a factor of the ionic concentration of the aqueous solution), and the SAP's functional polar groups that have an affinity for water. SAPs are typically made from the polymerization of acrylic acid blended with sodium hydroxide in the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAPs may be present in absorbent articles in particle or fibrous form.

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. For the purposes of this application, like features will be represented by like numbers between the figures. While not being expressly illustrated in every view or location, it should be understood that traditional absorbent article construction adhesive may be used between each of the various article layers, for securement of the layers within the article.

Generally speaking, in order to address the staining concerns perceived by consumers from potential pad leakage, to reduce fears of embarrassment from garment or bedding stains resulting from such leakage, and to reduce the effort necessary in removing stains that may actually occur on garments or bedding, the invention provides a feminine hygiene personal care absorbent article with a targeted decolorizing structure that can render menses stains and menses fluid colorless, or nearly so, within select portions of an absorbent article, before the fluid leaves the article. Such decolorizing structure is targeted since it is desirably in one embodiment, located in specific locations more lateral (although not necessarily in the same plane) to the absorbent core lateral edges. In some embodiments, such structures may also extend beyond the absorbent core front and back end edges. The decolorizing structures are in the form of projections or extensions, beyond either the lateral sides, front or back edges of the core layer(s), and are readily apparent when viewing the article in a cross-section along the D-axis. Such decolorizing structure can render such stain or menses fluid, clear or pale yellow, for example, so as to reduce potential staining risk to garments or bedding that may occur. With reduced stain potential, any leakage that actually does occur will be easier to remove. The invention also allows lower viscosity fluid to be directed to absorbent core layers for absorption and retention. Additionally, the invention provides decolorizing structures to impede menses flow off of the top surface, or from within interior layers and off the article lateral side edges, to reduce the visualization of an extensive article insult, when viewed from the article top surface. The invention provides regions of targeted decolorizing structure away from the core layer(s), which do not impede the direct absorption of menses fluid, once it has entered an absorbent layer (as they are generally present outside the central insult region/portion of the absorbent article), and which layers are positioned away, or directed laterally away from the absorbent layer(s), and projected laterally towards the product side edges, farther from the central longitudinal axis than the lateral side edges of the core layer(s). In one embodiment, decolorizing structures of the article are desirably positioned in or on at least one separate layer from the main absorbent core layer(s). Alternatively, such decolorizing structures may be present on extensions of the absorbent core layer(s). Still in a further alternative embodiment, such decolorizing structures may be positioned on multiple planar layers within the article, each desirably extending beyond the lateral side edge of the core layer(s) (more transverse when viewed along the D-axis).

Figure 1A:
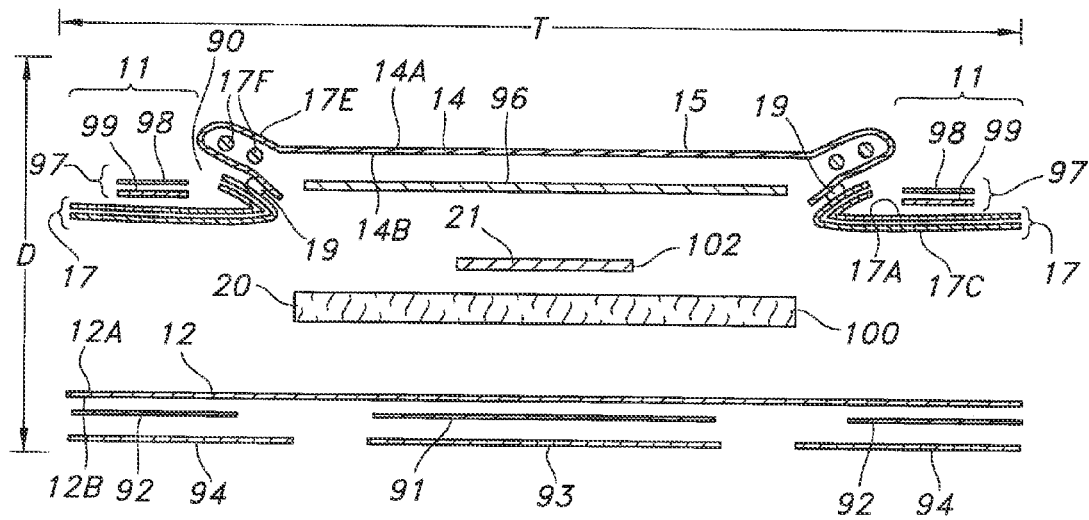
FIG. 1A is an exploded cross-sectional view of the feminine hygienic pad embodiment of FIG. 1 of the present invention taken along lines 1A-1A.
Figure 1B:
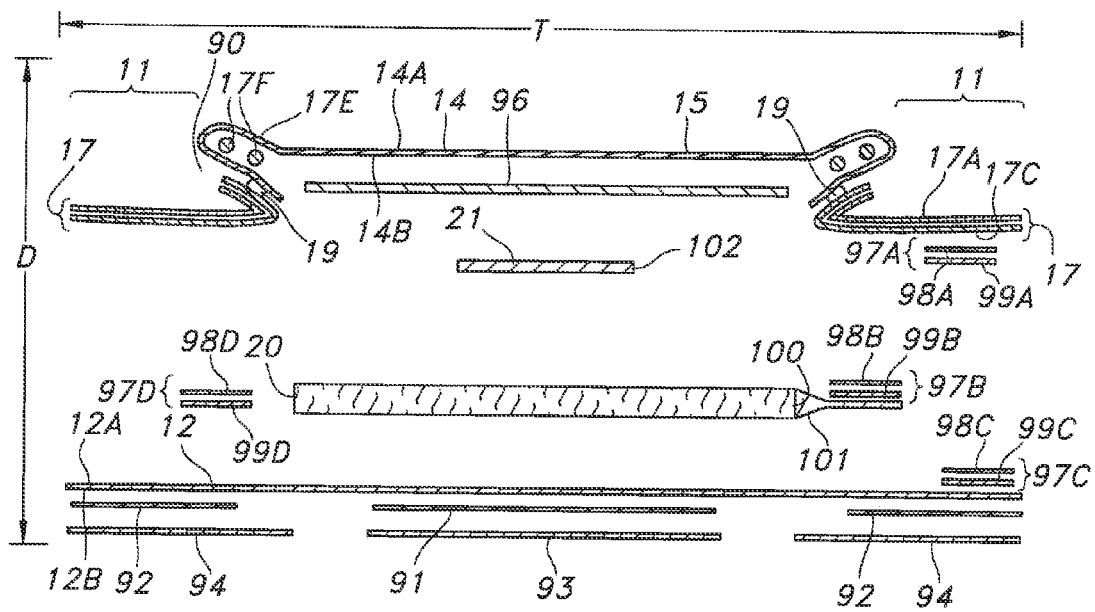
FIG. 1B is an exploded cross-sectional view of an alternative embodiment of the feminine hygienic pad of FIG. 1 of the present invention taken along lines 1B-1B.

More specifically, FIGS. 1 and 1A illustrate a top perspective and exploded cross-sectional view respectively, of a first embodiment of the present absorbent article invention in the form of a feminine hygienic pad. FIG. 1B illustrates an exploded cross-sectional view of an alternative embodiment of the pad of FIG. 1 taken along lines 1B-1B. FIG. 1B is meant to illustrate several of the various physical locations within a pad that the decolorizing structures 97 can be located.

The pad has a longitudinal axis (including the central longitudinal axis L shown, as indicated by a broken line), a transverse axis (and a central transverse axis T shown) and a depth direction (or Z-axis) D axis (as seen in FIG. 1A), which is the direction normal to the plane of the pad layers. The feminine hygienic pad (or feminine hygiene absorbent personal care article) 10 has side wings 11 extending laterally out at the longitudinally directed side edges 90 of the article, that are the lateral edges of the article. The feminine hygienic pad contains a liquid impermeable garment-facing backsheet layer 12 and a liquid permeable, user-facing top layer (e.g., topsheet layer) 14. The backsheet layer 12 and topsheet layer 14 sandwich at least one absorbent core layer 20. As illustrated in the embodiment of FIG. 1A, two absorbent core layers 20 and 21 are shown. While not expressly labeled, the topsheet layer 14 is shown as including optional embossing patterns in the form of waves/zig-zags, racetrack and arc patterns. The pad also includes a front and back end 23, 24 respectively.

The backsheet layer 12, being generally liquid-impermeable, is designed to face the inner surface, i.e., the crotch portion, of a user's undergarment (not shown) or outergarment. The backsheet therefore includes a core facing surface 12A and a garment facing surface 12B as seen in FIG. 1A. The backsheet layer 12 may optionally permit the passage of air or vapor out of the absorbent article 10, while still blocking the passage of liquids.

Any liquid-impermeable material may generally be utilized to form the backsheet layer 12. For example, one suitable material that may be utilized is a microporous polymeric film, such as a polyolefin film of polyethylene or polypropylene. In particular embodiments, a polyethylene film is utilized that has a thickness in the range of about 0.2 mils to about 5.0 mils, and particularly between about 0.5 to about 3.0 mils. A specific example of a backsheet layer material is a polyethylene film such as that obtainable from Pliant Corporation, Schaumburg, Ill., USA. Another example would include calcium carbonate-filled polypropylene film. In still a further embodiment, the backsheet may be a hydrophobic nonwoven material with water barrier properties such as a nonwoven laminate, an example of which would be a spunbond, meltblown, meltblown, spunbond (or SMMS), four layered, laminate. The backsheet layer 12 may therefore be of a single or multiple layered construction, such as of multiple film layers (a core and one or more skin layers), multiple nonwoven layers, or laminates of film and nonwoven or woven fibrous layers. Even with a film backsheet, a nonwoven fibrous layer may be desirably used as the garment facing surface 1213 for better "hand" or feel.

The topsheet layer 14 may surround the absorbent core layer(s) 20 so that it completely encases the absorbent core layer(s) and/or backsheet layer (encasement not shown). Alternatively, the topsheet layer 14 and the backsheet layer 12 may both extend beyond the absorbent core layer(s) 20, 21 lateral-most edges (100, 102 for example) and front and back end edges, and be peripherally joined together to form a sealed peripheral edge, either entirely or partially, using known attachment techniques. Typically, the topsheet layer 14 and the backsheet layer 12 are joined by adhesive bonding, ultrasonic bonding, thermal bonding or any other suitable joining method known in the art, the sealed edges defining an overall sealed peripheral edge 16 of the feminine hygienic pad 10. The feminine hygienic pad 10 and internal layers may be of various shapes and geometries but will generally have opposite lateral sides 90 (extending along the product longitudinal direction) and longitudinally directed front and back ends 23, 24.

The topsheet layer 14 is generally designed to contact the body of the user and is liquid-permeable. The liquid permeable topsheet layer 14 has an outwardly directed user facing surface 14A that may directly contact the body of the wearer and receive bodily exudates, and an absorbent layer, facing surface 14B as seen in FIG. 1A. The topsheet layer 14 is desirably provided for comfort and conformability and functions to direct bodily exudates away from the body of a user, through its structure and towards the absorbent core fayer(s) 20. The topsheet layer 14 desirably retains little or no liquid in its structure, so that it provides a relatively comfortable and non-irritating surface next to the tissues within the vestibule of a female wearer. A user of the feminine hygiene pad would generally view any appearing stain within, or on the pad, by viewing the topsheet layer 14 user facing surface 14A.

The topsheet layer 14 can be constructed of any woven, nonwoven or sheet material which is easily penetrated by bodily exudates which then may be absorbed by the core layer(s) or come in contact with the core-facing surface of the backsheet layer 12A. Examples of suitable topsheet materials include natural fiber webs (such as spunlaced cotton), rayon, hydroentangled webs, bonded carded webs of polyester, polypropylene, polyethylene, nylon, or other heat-bondable fibers (such as bicomponent fibers), polyolefins, such as copolymers of polypropylene and polyethylene, linear low-density polyethylene, and aliphatic esters such as polylactic acid. Finely perforated films and net materials can also be used as a topsheet layer 14, as can laminates of/or combinations of these materials. A specific example of a suitable topsheet material is a bonded carded web made of polypropylene and polyethylene such as that obtainable from Sandler Corporation, Germany. U.S. Pat. No. 4,801,494 to Datta, et al. and U.S. Pat. No. 4,908,026 to Sukiennik, et al. teach various other topsheet materials that may be used in the present invention, each of which is hereby incorporated by reference in its entirety. The topsheet layer 14 may also contain a plurality of apertures (not shown) formed therethrough to permit body fluid to pass more readily into the absorbent core layer(s) 20. The apertures may be randomly or uniformly arranged throughout the topsheet layer 14, or they may be located only in a narrow longitudinal band or strip arranged symmetrically about the central longitudinal axis L of the feminine hygienic pad 10. The size, shape, diameter and number of apertures may be varied to suit an article's particular use.

As previously noted, the topsheet layer 14 may also be embossed with any desired embossing pattern to define embossed channels. Embossing techniques are well known to those skilled in the art. An embossing pattern not only creates an aesthetically pleasing surface, but the channels may also facilitate intake and/or distribution of menses fluid. Menses will tend to flow along the densified edges of the channels rather than pool on contact points of the topsheet layer 14.

The topsheet layer 14 itself may be formed from one layer across the user-facing surface, or alternatively from more than one separate layers in a side-by-side arrangement, desirably along the article longitudinal axis, as will be further described in connection with FIG. 1A, Desirably, in one embodiment, the topsheet layer 14 has a basis weight of between about 15 gsm and 100 gsm.

In one embodiment, as seen in the cross-sectional view of FIG. 1A, taken along lines 1A-1A of FIG. 1, a topsheet layer 14 is constructed of at least two different materials 15, 17 in an overlapping, but substantially side-by-side arrangement along the longitudinal axis. The two different materials are a central longitudinally directed topsheet material 15 and longitudinally directed side edge topsheet materials 17. Such a dual-layer construction is generally described in U.S. Pat. No. 5,961,505 to Coe, U.S. Pat. No. 5,415,640 to Kirby and U.S. Pat. No. 6,117,523 to Sugahara, each of which is incorporated by reference herein in its entirety. Such dual-layer construction is often also referred to as a dual cover, two-layer topsheet, bicomponent topsheet, or a hybrid cover construction. With specific reference to FIG. 1A, in one embodiment, a central longitudinally directed topsheet material 15 is positioned symmetrically about the product's central longitudinal axis L of the topsheet layer 14. Such central longitudinally directed topsheet material 15 is desirably in one embodiment, a through-air bonded carded web material (TABCW) having a basis weight of between about 15 and 100 gsm. Previously described nonwoven, woven and perforated/apertured film topsheet materials may also be used as the central longitudinally directed topsheet material 15 of the two-layer, topsheet layer 14. In one embodiment, such central longitudinally directed topsheet material is constructed from TABCW having a basis weight of between about 20 and 50 gsm, which material is readily available from nonwoven material manufacturers, such as Xiamen Yanjan Industry, Beijing DaYuan Nonwoven Fabrics and others. Alternatively, apertured films, such as those available from such film suppliers as Texol and Tredegar may be employed. Different nonwoven, woven or film sheet materials may be used as the longitudinally directed side edge topsheet materials 17, adjacent and bonded to the central longitudinally directed topsheet material 15. The selection of such topsheet layer 14 materials will vary based on the overall desired attributes of the topsheet layer. For example, it may be desired to have a hydrophilic material along the central longitudinal axis L and hydrophobic barrier-type materials along the longitudinally directed side edges to prevent leakage and increase a sensation of dryness at those longitudinally directed side edges 90. Such longitudinally directed side edge materials 17 may be either adhesively, thermally, ultrasonically or otherwise bonded 19 to the central longitudinally directed topsheet material 15 along or adjacent the longitudinally directed side edges of the materials (such as on the user facing surface 14A (shown in FIG. 1A) or on the absorbent core layer facing surface 14B (not shown)) of the central longitudinally directed topsheet material 15. Traditional article construction adhesive may desirably be used to bond the longitudinally directed side edge topsheet materials 17 to the central longitudinally directed topsheet material 15. Either of the topsheet materials in a dual-cover topsheet construction may be treated with surfactants or skin-health benefit agents, as are well known in the art.

Such longitudinally directed side edge topsheet materials 17 may themselves be of a single or multiple-layered construction. In one embodiment, such longitudinally directed side edge topsheet materials 17 are themselves adhesively or otherwise bonded laminates. In one embodiment, for example, such longitudinally directed side edge topsheet materials 17, are constructed of an upper fibrous nonwoven layer 17A, such as a spunbond material, laminated to a bottom layer 17C of a hydrophobic barrier film material. Such a spunbond layer may be formed from a polyolefin, such as a polypropylene and include a wetting agent if desired. In one embodiment, such spunbond layer is between 10 and 70 gsm, desirably between about 12 and 30 gsm, and treated with hydrophilic wetting agents. Such film layer may be apertured to allow fluid to permeate to lower layers, and may be either of a single layer or multiple layer construction. Desirably, such film is a polyolefin, such as a polyethylene having a basis weight of between about 10 and 40 gsm. Construction adhesive may be used to laminate the spunbond layer to the film layer at an add-on level of between about 0 and 15 gsm. When a film barrier layer 17C is used in the overall topsheet design, it may include opacifying agents, such as film pigments, that help the film in masking stains along or adjacent to, the pad's side edges 90, thereby serving as a masking element. In such a fashion, the film layer would serve to limit visualization of a menses insult stain along the pad side edges when viewed from above the user facing surface 14A of the topsheet layer 14. The film layer may also serve as a barrier layer to prevent rewet of the topsheet layer user-facing surface, as well as to prevent the flow of menses off the side edges of an article. The central longitudinally directed topsheet material 15 may in one embodiment wrap around longitudinally directed elastic strands or shrinkable fibers 17F and be bonded to longitudinally directed side edge topsheet materials 17 via at least bond points or bond lines 19. The longitudinally directed side edge topsheet materials 17 may also be laminates such as a spunbond-meltblown-meltblown-spunbond layer (SMMS) laminate, spunbond-film laminate, or alternatively, other nonwoven laminate combinations.

A decolorizing structure 97 is in one embodiment, desirably placed atop the longitudinally directed side edge topsheet materials 17. Such decolorizing structure extends along the transverse axis in one embodiment, to the wings 11 as illustrated, and is of a length such that it frames much of the absorbent core layer along the absorbent article side edges 90. Alternatively, such decolorizing structure is of a length 18, such that it frames the absorbent core layer(s) at the wing 11 area. In a further embodiment, the decolorizing structure 97 extends out over the wings 11 such that the topsheet layer material on the wing structures 11 also includes the decolorizing structure. In any event, it is desirable for such decolorizing structure to extend a width along the transverse axis to a position that is more lateral than the lateral-most edge of the absorbent core layer in a plane beneath it (100), when viewed in a cross-section along the D-axis (as seen in FIG. 1A). As can be seen in FIG. 1A, the decolorizing structure 97 extends more laterally than the lateral most edges 100, 102 of both the core layers 20, 21. The overall width of the decolorizing structures along the transverse axis (from one to the other), including the space between the two structures along the transverse axis, is larger than the width of either of the absorbent core layers. Such decolorizing structures are closer to the pad outer lateral edges than the absorbent core layer(s). It is desirable that a decolorizing structure be positioned along or adjacent each lateral edge of the article, but such a structure may be positioned along only one edge 90. In one embodiment, such decolorizing structure 97 (s) is positioned on one or more separate layers within a pad/absorbent article, such that one or more layers include a decolorizing structure along or adjacent the edge(s) 90. Such decolorizing structures may be in the form of lateral projections (as shown in FIG. 1A on top of the topsheet material) or extensions from the topsheet layer, surge layer, core layer, other pad interior layer, or even the core facing surface 12A of the backsheet layer 12. Such decolorizing structure 97 may include a color different from that of the overall article color or underlying layer color. Such different color can serve as a visual indication of additional product functionality in targeted regions, or can enhance the layer's feature as a masking element within the article. Such decolorizing structures desirably accomplish multiple purposes, those being filtration of the coloring components of menses and prevention of stain spread to the article side edges; providing barrier protection along the article side edges; providing direction of fluid to absorbent core layers, and masking of stains.

In a desirable embodiment, such decolorizing structures are laminates of a hydrophilic layer with a hydrophobic layer. Such hydrophilic layer can be a surfactant treated nonwoven layer or laminate material, such as one or more layers of meltblown, airlaid or spunlace material for example that has been treated with a surfactant, so as to make it more accepting to menses and menses components. Such hydrophobic layer can be a layer or laminate of fibrous polyolefinic nonwoven materials such as for example a spunbond-meltblown-spunbond (SMS) or SMMS laminate, or alternatively, a film sheet, such as a polyolefinic film layer or layers. Such hydrophilic and hydrophobic materials are desirable laminated using thermo or adhesive bonding. In one example, the hydrophilic layer can be a microfiber meltblown layer (MBMF) and the hydrophobic layer can be a polymeric film. In such an example, construction adhesive is desirably used to laminate the meltblown microfiber layer at an add-on of between about 1 and 5 gsm, and the film barrier layer is desirably a polyolefin film of a basis weight of between about 10 and 40 gsm. While it is desirable for the dimensions of each hydrophilic and hydrophobic materials to be the same in the width and length directions, such need not be the case, such that one facing side of the laminate may include both hydrophilic and hydrophobic portions, In another embodiment, the hydrophobic material may be partially wrapped about the hydrophilic material to achieve a surface with both hydrophilic and hydrophobic portions. In one embodiment, it is desirable for the hydrophobic surface of the laminate to face the backsheet layer of the article. Such a placement helps to prevent rewet of the topsheet layer, and also wetness from the core from being transferred to the hydrophilic surface of the laminate (facing the user). In one embodiment, one or more layers of the laminate may be printed to enhance a stain masking effect, using known printing methods. Such printing may also provide additional visual cues as to the functionality of the decolorizing structures. In one embodiment, it is desirable to place decolorizing structures along each lateral side edge 90 of a pad between 20 and 100 mm apart, more desirably between 30 and 80 mm apart. As will be later described, in some contemplated embodiments, the decolorizing structures are desirably placed between the topsheet layer 14 and the absorbent core layer 20. So as to avoid unwanted transfer of insult from the core layer(s) to the decolorizing structure(s), in some embodiments it is desirable to place a hydrophobic layer between the decolorizing structures and the core layer(s), or to alternatively place the hydrophobic layer of the described laminate in a position that faces the core layer 20, In one embodiment, the decolorizing structure 97 is a laminate of a first nonwoven strip 98 that is laminated to a second nonwoven strip 99. The lamination may be accomplished by heat calendering, but desirably by adhesive lamination. The first nonwoven strip 98 desirably has a pore size range of between about 20 and 1000 microns, an average pore size range of about 50-200 microns, and an average fiber diameter size of between about 2 and 20 microns. It desirably has a basis weight of between about 10 and 70 gsm. In one embodiment, such first nonwoven strip is of a spunbond material having a basis weight of between about 12 and 30 gsm. It is desirable that such spunbond material be of a polyolefin such as polypropylene, polyethylene or a combination thereof. Such material may be treated, such as by hydrophilic wetting agents. The second nonwoven strip 99 desirably has a pore size range of between about 1 and 100 microns, having an average pore size of about 3-40 microns, and an average fiber diameter size of between about 0.2 to 10 microns. It desirably has a basis weight of between about 10 and 100 gsm. It is further desirable for the average pore size ratio between the first nonwoven strip material 98 and the second nonwoven strip material 99 to be between about 1:1 to about 1:0.01. The average pore size ratio would be the ratio of the average pore size of the strip closest to initial menses contact, to the average pore size of the strip farthest from initial menses contact. For example, if such a deodorizing structure was positioned on the topsheet, the strip closest a user would be closest to the initial menses contact. If a decolorizing structure is positioned under a permeable longitudinally directed side edge topsheet material 17, the strip closest to initial menses contact would be closest to the longitudinally directed side edge topsheet material 17. Such a configuration is described in FIG. 1B at 97A.

In one embodiment such second nonwoven strip is of a meltblown material having a basis weight of between about 10 and 100 gsm. It is desirable that such meltblown material be of a polyolefin such as polypropylene. Such material may be treated, such as by hydrophilic wetting agents. The second nonwoven strip is in one embodiment desirably a meltblown microfiber (MBMF) polypropylene material, desirably between about 10 and 100 gsm in basis weight, more desirably between about 20 and 50 gsm, even more desirably between about 20 and 30 gsm, having an average fiber size of desirably between about 1 and 10 microns in diameter. In one embodiment, the meltblown polypropylene microfiber material is treated with wetting agents for adequate handling of aqueous fluids such as menses. Examples of such wetting agents include surface active agents (or surfactants) having a hydrophilic lipophilic balance (HLB) of at least 6, preferably between 7 and 18. Definitions of "surfactant" and "HLB scale" can be found in textbook "Introduction to Colloid and Surface Chemistry", by Duncan J Shaw, $4^{th}$ edition, 1992, published by Butterworth-Heinemann. Ltd. A variety of surfactants can be used and include those that are anionic, cationic or neutral from a charge standpoint. Mixtures of surfactants and other wetting agents can also be used. Typical wetting agent add-on can range between, about 0.1 to 10 wt %, preferably between 0.2 to 5% by weight of the substrate. However, add-on levels higher than 10 wt % can also be used. The MBMF may be treated to impart hydrophilicity by either Aerosol GPC of Cytec, or alternatively, Ahcovel Base N-62 for example. Such material is available from Yuhan-Kimberly Ltd., Seoul, Korea and FiberTex, Malaysia.

The nonwoven strips 98 and 99 desirably have the same overall dimensions as each other. In one embodiment the strips are desirably between about 5 to 60 mm in width along the pad's transverse axis/direction, such as to extend laterally out to cover both the pad longitudinal side edges 90 and a portion of the wings 11. It is desirable that such strips extend the entire length of the article, but a shorter length is also contemplated, as illustrated in FIG. 1 at 18. Such shorter strips in an alternative embodiment, would extend along the side edges on the topsheet layer 14 or other layers, between about 30 and 99 percent of the length of the article.

While it is desirable to add such strips along the side longitudinal edges of the pad/article as shown at 97, they can in an alternative embodiment, be added in shortened lengths across the front and back ends of the article in the transverse direction 22, such as added to the topsheet layer 14 user-facing surface 14A, at the article front 23 and back 24 ends, to reduce leakage stain potential from these ends of the pad/article. In still a further alternative embodiment, they may be added along all peripheral side edges of the article, such as along the peripheral side edges of the topsheet layer 14. By adding additional decolorizing structures in these side edge locations, either in this embodiment or in the embodiments which follow, a structure which encourages overall fluid flow to the central absorbent core is also created. Such a configuration keeps the decolorizing structure out of the central insult region/portion of the article.

Alternatively, rather than place the strips as projections above the topsheet layer material as shown in FIGS. 1 and 1A, such strips may be placed below the topsheet layer materials in various locations, as seen in FIG. 1B. For example such decolorizing structures 97D (such as laminated strips 98D, 99D in FIG. 1B) can be placed between the backsheet layer 12 and the topsheet layer 14, and in the same general transverse axis locations (as 97) but lateral to the core side edge. The D-axis location would be changed. Such strips need not be connected to a layer of the same plane, but instead may be held in place by being sandwiched between layers in adjacent planes (adjacent planes along the D-axis), or alternatively by being bonded to the lower or upper surfaces of layers in adjacent planes. For example, such decolorizing structures 97A (laminate of 98A and 99A), 97C (laminate of 98C and 99C) may be bonded to the garment facing surface of the topsheet layer or the core facing surface of the backsheet layer at a location more lateral than the lateral side edges of the absorbent core layer along the transverse axis, Alternatively, the absorbent core layer 20 may be wrapped in a core wrap 101 that extends laterally beyond the core edge 100 and the decolorizing structures 97B (laminated strips of 98B and 99B) can be bonded to the extending core wrap 101. Such core wrap material may be a tissue or polymeric nonwoven material. While these various decolorizing structure locations have all been shown for ease of reference in one figure, it should be appreciated that one or more of these placement locations may be employed for such structures in any given pad/article. As also previously noted, it is desirable for such decolorizing structures to be placed in pairs within an article, each along the lateral side edges of an article, symmetrically about the central longitudinal axis L, and in a position more lateral completely (such as 97, 97A, 97B, 97C, 97D in FIG. 1B), than the lateral most edges of the absorbent core layer(s), or at least partially more lateral (such as 97 in FIG. 1C, 1D) than the lateral most edges of the absorbent core layer 20, when viewed from a cross-sectional view. In such embodiments, the decolorizing structures may overlap somewhat, the absorbent core layer when viewed along the D-axis (and transverse axis), with some portion of the decolorizing structures extending beyond the lateral edge 100 of the absorbent core layer 20 towards the article side edge.

In cases where such laminated strips (the decolorizing structures) are placed under the topsheet layer, such as those illustrated in FIG. 1B, it is also contemplated to use different materials for the laminate strips to achieve similar benefits as described above. An example of such different materials include a meltblown layer (or similar material) laminated to a film layer or other type of nonwoven layer which acts as a barrier layer to liquid. In such example, the meltblown layer portion of the laminate will be in contact with the longitudinally directed side edge topsheet material 17, and the barrier material may partially be in contact with the absorbent core layer 20. In this fashion, if the longitudinally directed side edge topsheet material 17 is a nonwoven layer, it will perform a similar function as the top layer 98 of the laminate in FIG.

1A, while the film or other nonwoven barrier layer facing the absorbent core layer, will prevent the undesired transfer of fluid from the absorbent core layer to the laminate structure 97.

As seen in FIG. 1A, in one embodiment, such topsheet layer 14 may include topographical features 17E which extend out of the overall plane (along the D-axis) of the topsheet layer 14, and which result from side portions of the central topsheet material rising above the generally planar topsheet surface, either as a result of contracted elastic strands, or shrinkable fiber yarns 17F that are laminated to the topsheet layer 14 along the longitudinal axis, and which shrink upon lamination or alternatively, during contact with menses/moisture. Such strands or yarns, while being shown in two locations in the figure, may be placed in several (typically parallel) longitudinally directed configurations, across the transverse axis of the pad/article topsheet. Such a configuration is described for example, in U.S. patent publication 20100152690 to Ong, which is hereby incorporated by reference in its entirety. Such shrinkable fibers may be made from polyvinyl alcohol (PVA) polymer available from a number of polymer vendors, such as Kuraray.

The feminine hygienic pad 10 of FIGS. 1 and 1A also contains at least one absorbent core layer 20 positioned between the topsheet layer 14 and the backsheet layer 12, that provides capacity to absorb and retain bodily exudates. The absorbent core layers 20, 21 may be selected so that it/they demonstrate a particular total absorbency capacity, depending on the article type. For example, for feminine care products, the total absorbency capacity can typically be within the range of about 7-50 grams of menstrual fluid, and can more typically be within the range of about 30-40 g of menstrual fluid. Within the feminine hygiene absorbent personal care article category, it may be desirable to have different levels of absorbency capacity depending on product type. For example, feminine care panty liners are typically used by consumers for "light" menstrual flow days, feminine hygiene pads are typically used by consumers for "regular" menstrual flow days, and feminine care oversized pads are typically used by consumers for "overnight" timespans, or "heavy" menstrual flow days. It may be desirable for feminine care liners to have in one embodiment, an absorbency capacity of between about 1 and 5 grams of fluid. For feminine hygiene pads, it may be desirable in one embodiment, to have an absorbency capacity of between about 10 and 30 grams of fluid. For feminine hygiene oversized pads, in one embodiment it may be desirable to have an absorbency capacity of between about 20 and 50 grams of fluid.

The absorbent core layer(s) can generally be any single layer structure or combination of layer components, which desirably demonstrate some level of compressibility, conformability, are non-irritating to a wearer's skin, and capable of absorbing and retaining liquids and certain other body wastes. For example, the absorbent core layer(s) 20 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In a particular embodiment, the absorbent web material is a matrix of cellulosic fluff, and may also include superabsorbent material. The cellulosic fluff may comprise a blend of wood pulp fluff. One desirable type of fluff is identified with the trade designation NB 416, available from Weyerhaeuser Corp., and is a bleached, highly absorbent wood pulp containing primarily soft wood fibers. The absorbent materials may be formed into a web structure by employing various conventional methods and techniques. For example, the absorbent web may be formed with a dry-forming technique, an air forming technique, a wet-forming technique, a foam-forming technique (making a foam or foam-like structure), or the like, as well as combinations thereof. A coform nonwoven material may also be employed. Methods and apparatus for carrying out such absorbent core layer manufacturing are well known in the art.

Such core layer(s) may be wrapped in tissue or nonwoven sheeting, as previously described 101 for integrity or to hold in place SAP materials. The core layer 20 may be immediately adjacent the topsheet layer 14, or alternatively adjacent an intermediate core layer 21, transfer layer, distribution layer, surge layer or combination thereof. For example, an additional airlaid core layer 21 might be desirable. The shape of the core layers from a top plan view (not shown) are desirably a rectangular, racetrack or dogbone shape, as is known in the art. The core layer may alternatively be a superabsorbent polymer (SAP)-containing compressed sheet. Desirably, such superabsorbent polymer-containing sheet is a fluff-based material that is a combination of pulp and SAP enclosed with a tissue carrier and having a basis weight of between about 40 and 400 gsm. It should be recognized that individual layers of a multilayered absorbent core may be bonded using traditional bonding techniques such as thermal, ultrasonic or adhesive processes, within the core layer itself, and bonded or otherwise held in place, using any of such methods to the remaining absorbent article structure.

With reference again to FIG. 1A, subjacent the backsheet layer 12 along the D axis, and along the garment facing surface 12B, are desirably placed garment fastening adhesive patches 91 and 92. The garment adhesive patch 91 is situated along the pad central longitudinal axis of the garment facing surface of the backsheet, for fastening the article directly to the crotch portion of an undergarment. The two side wing adhesive patches 92 are positioned under the wings 11, also on the garment facing surface of the backsheet.

Adhesive peel/release sheets 93, 94 are positioned respectively over the garment adhesive patch 91, and the wing adhesive patches 92.

The feminine hygiene pad 10 may also contain additional internal/interior layers. For example, in one embodiment, the feminine hygiene pad 10 may contain a liquid-permeable intake layer positioned between the topsheet layer 14 and the absorbent core layer 20. As seen in FIG. 1A, the feminine hygiene pad 10 includes an additional absorbent airlaid layer 21. Such an intake layer may be made of a material that is capable of rapidly transferring, in the D-axis/direction, body fluid that is delivered to the topsheet layer 14. The intake layer may generally have any shape and/or size desired. In one embodiment, the intake layer has a rectangular shape, with a length equal to or less than the overall length of the feminine hygienic pad 10, and a width less than the width of the feminine hygienic pad 10. For example, a length of between about 150 mm to about 300 mm and a width of between about 10 mm to about 60 mm may be utilized. Any of a variety of different materials are capable of being used for the intake layer to accomplish the above-mentioned functions. The material may be synthetic, cellulosic, or a combination of synthetic and cellulosic materials. For example, airlaid cellulosic tissues may be suitable for use in the intake layer. The airlaid cellulosic tissue may have a basis weight ranging from about 10 gsm to about 300 gsm, and in some embodiments, between about 100 gsm to about 250 gsm. In one embodiment, the airlaid cellulosic tissue has a basis weight of about 200 gsm. The airlaid tissue may be formed from hardwood and/or softwood fibers. An airlaid tissue has a fine pore structure and provides an excellent wicking capacity, especially for menses.

Additional layers between the topsheet layer 14 and the core layer 20 include liquid-permeable transfer delay layers or surge layers as previously noted. Still another layer that may be present between the topsheet layer and the absorbent core layer includes a bicomponent fluid distribution layer (BFDL) 96, which increases absorbency by providing a high void space and may be made of a TABCW, having a basis weight in one embodiment of between about 25 and 100 gsm.

While side wings 11 are shown as formed from lateral extensions of the backsheet 12 and the topsheet 14 such that they are integral portions of the pad 10, they may also be laterally-attached, non-integral structures.

Figure 1C:
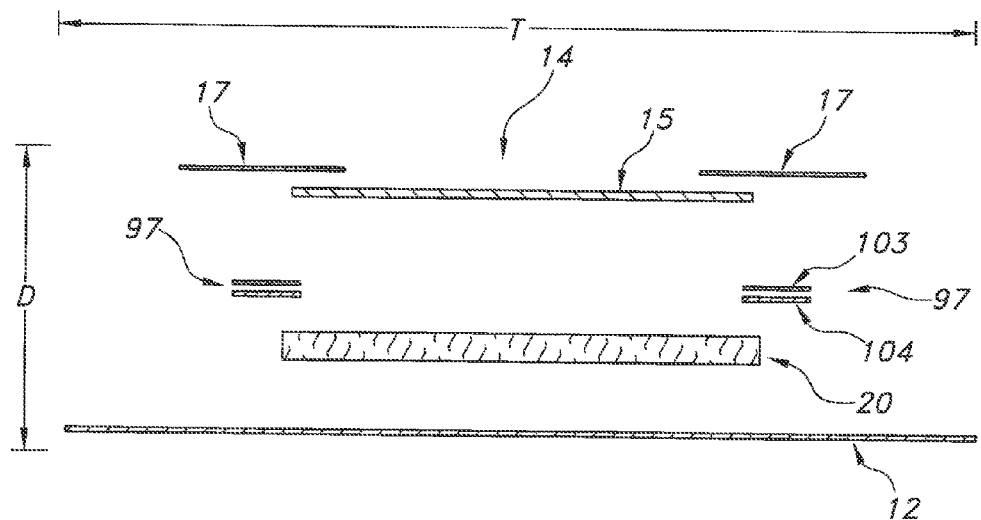
FIG. 1C is an exploded cross-sectional view of an alternative embodiment of the feminine hygienic pad of FIG. 1 of the present invention, taken at approximately lines 1C-1C.

In an alternative embodiment, as shown in an exploded cross-section view in FIG. 1C (taken approximately at line 1C-1C) of FIG. 1, the absorbent article is in the form of a feminine hygienic pad with a topsheet layer 14 that is of a dual cover construction having two different material components 15, 17. The decolorizing structure 97 is positioned beneath the topsheet layer 14, along the D-axis, and between the topsheet layer 14 and the absorbent core layer 20. The decolorizing structure in this embodiment includes a laminate of a nonwoven strip 103 to a film strip 104. Desirably, as in previous embodiments, the nonwoven strip is a meltblown microfiber layer. The film strip is desirably a polyethylene film. The layers are desirably adhesively laminated. As previously noted, the decolorizing structure 97 extends more laterally than the lateral most edge 100 of the absorbent core layer 20 (relative to the side edges of the feminine hygiene pad). It is desirable in one embodiment for the lower layer of the laminate, that is the layer facing the core layer, to be a hydrophobic barrier layer, which can also assist in masking stains which appear along the article side or core side areas. In such an instance, the lower layer may also be a hydrophobic fibrous nonwoven barrier layer, rather than a film layer.

Figure 1D:
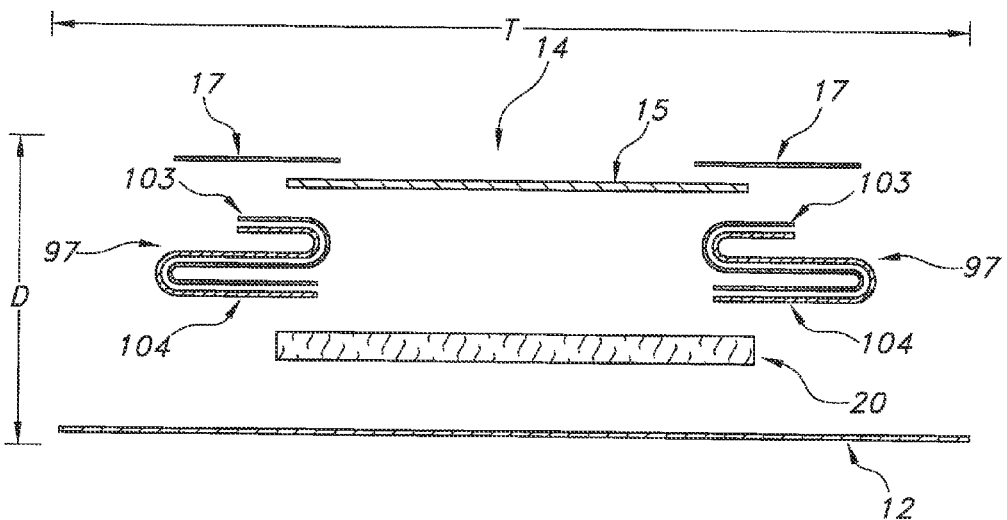
FIG. 1D is an exploded cross-sectional view of an alternative embodiment of the feminine hygienic pad of FIG. 1 of the present invention, taken at approximately lines 1D-1D.

In still a further alternative embodiment, as shown in an exploded cross-section view in FIG. 1D (taken approximately at line 1D-1D), the decolorizing structure 97 of FIG. 1C is folded in addition to being laminated such that it takes on an "S" and reverse "S"-like configuration. In this fashion the nonwoven layer 103 is facing the topsheet layer 14 and the film layer 104 is facing the core layer. Menses can travel around the S configuration on the nonwoven layer 103, but not between the S features directly, because of the film barrier layer. Such a construction serves to create both a masking element (in the form of the film 104), as well as a filtering structure for filtering menses colorants (in the form of the nonwoven layer 103), As with prior embodiments, the decolorizing structure 97 extends at least partially beyond the lateral most edge of the absorbent core layer 20 along the transverse direction. It should be recognized that the folded decolorizing structures may include one fold (such as in a "U" shape), two folds (as in an "S" shape), three folds, (as in an "M" shape) or more folds. Desirably, the folded decolorizing structures include ends which terminate towards the central longitudinal axis of the pad/article, rather than towards the lateral side edges of the article. By placement of the ends of the folded decolorizing structures facing towards the central longitudinal axis of the article, fluid which wicks along the decolorizing structures eventually is deposited onto the absorbent core layer (beneath it along the D-axis), As described herein, such decolorizing structures may be placed above the topsheet layer 14, or below the topsheet layer 14. Such folded structures are held in place via adhesive, and are not freely expandable as an accordion, and therefore do not allow the absorbent core layers or other layers to float or move within the article.

Figure 1E:
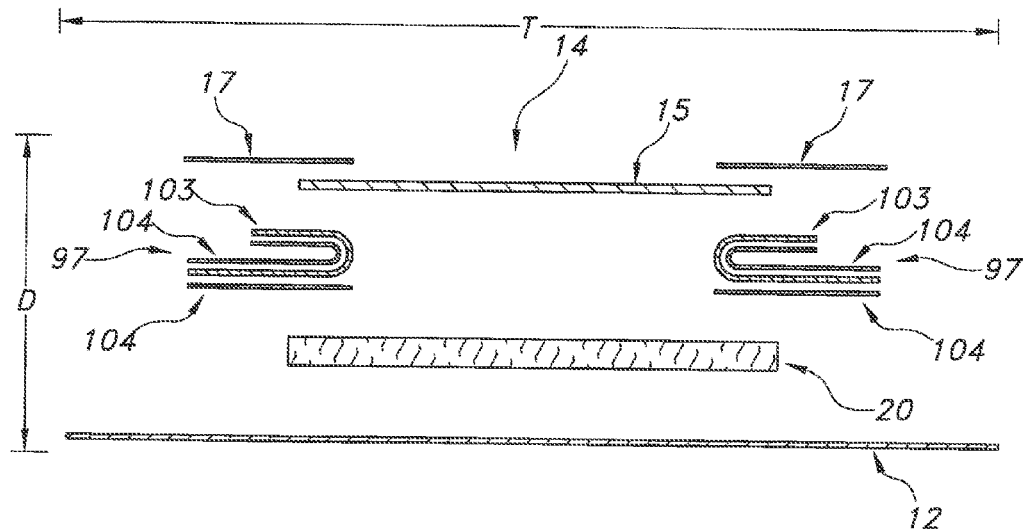
FIG. 1E is an exploded cross-sectional view of an alternative embodiment of the feminine hygienic pad of FIG. 1 of the present invention, taken at approximately lines 1E-1E.

In an alternative embodiment, as shown in exploded cross-sectional view in FIG. 1E, such "U"-shaped folded decolorizing structures 97 may include a hydrophilic nonwoven material 103 laminated to a hydrophobic barrier material 104 on two sides, such that a hydrophobic barrier layer separates the decolorizing structure from the absorbent core layer 20. In this fashion, insult fluid within the absorbent core layer 20 is prevented from passing to the decolorizing structures 97.

Figure 1F:
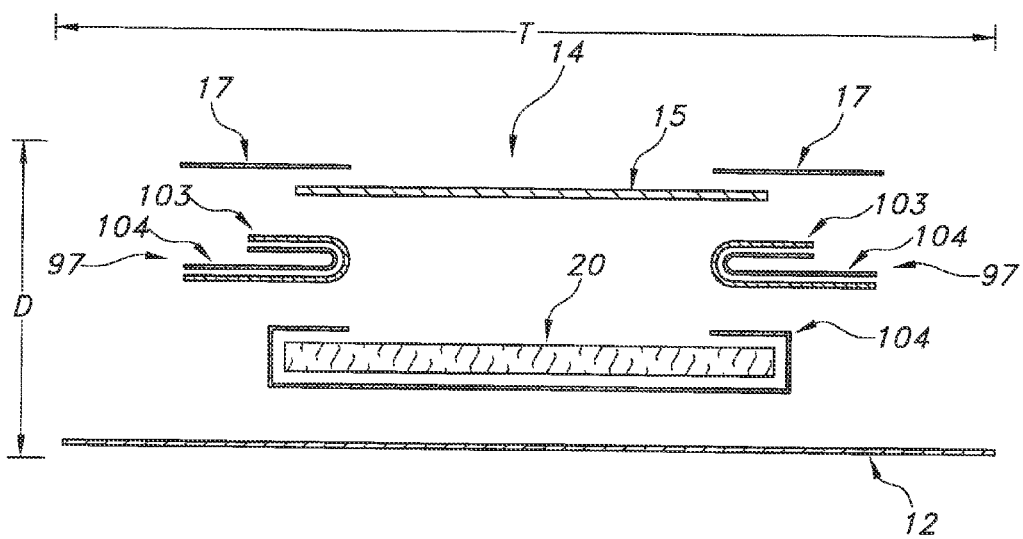
FIG. 1F is an exploded cross-sectional view of an alternative embodiment of the feminine hygienic pad of FIG. 1 of the present invention, taken at approximately lines 1F-1F.

In still a further alternative embodiment, as shown in exploded cross-sectional view in FIG. 1F, such "U"-shaped folded decolorizing structures 97 include only a hydrophilic nonwoven material 103 laminated to a hydrophobic barrier material 104, but the decolorizing structure 97 is separated from the absorbent core layer 20 by another hydrophobic barrier material layer 104 which only partially envelopes the absorbent core layer 20.

Figure 1G:
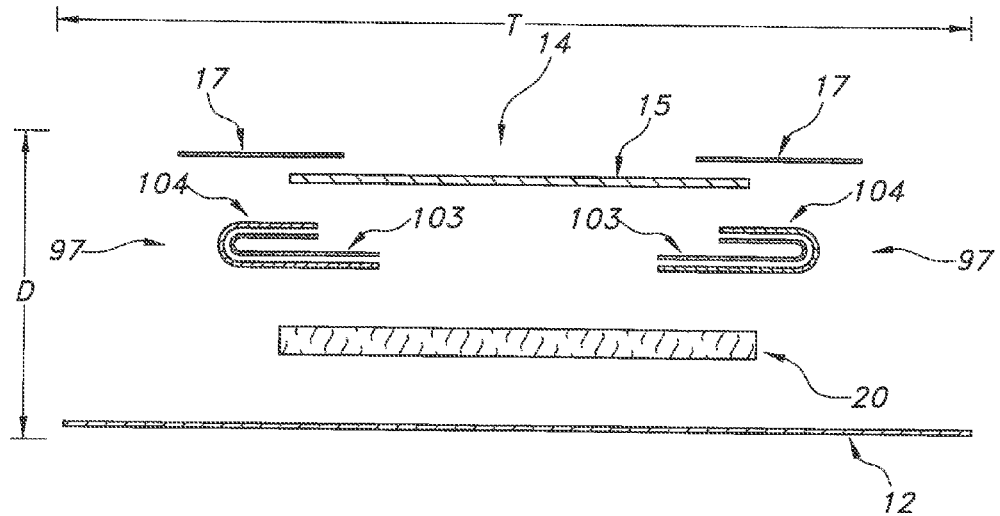
FIG. 1G is an exploded cross-sectional view of an alternative embodiment of the feminine hygienic pad of FIG. 1 of the present invention, taken at approximately lines 1G-1G.
Figure 1H:
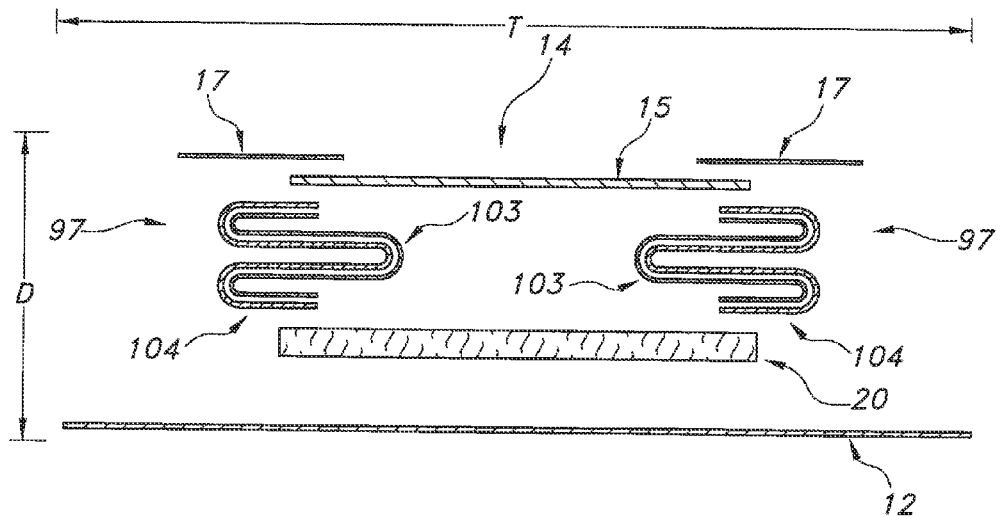
FIG. 1H is an exploded cross-sectional view of an alternative embodiment of the feminine hygienic pad of FIG. 1 of the present invention, taken at approximately lines 1H-1H.

In still a further alternative embodiment, as shown in exploded cross-sectional view in FIG. 1G, such "U"-shaped folded decolorizing structures 97 include only a hydrophilic nonwoven material 103 laminated to a hydrophobic barrier material 104, but the decolorizing structures 97 are inverted from those illustrated in FIGS. 1E and 1F such that the ends of the laminate layers 103 and 104 are positioned over the core layer 20. In this fashion, any menses which wicks along the hydrophilic nonwoven layer 103 will be directed to the absorbent core layer 20 beneath it along the D-axis. In a similar fashion, as illustrated in exploded cross sectional view in FIG. 1H, a 3 folded, "M" shaped decolorizing structure 97 is positioned adjacent each lateral side edge of the pad/absorbent article, extending more laterally than the absorbent core layer 20 lateral-most edge.

Figure 1I:
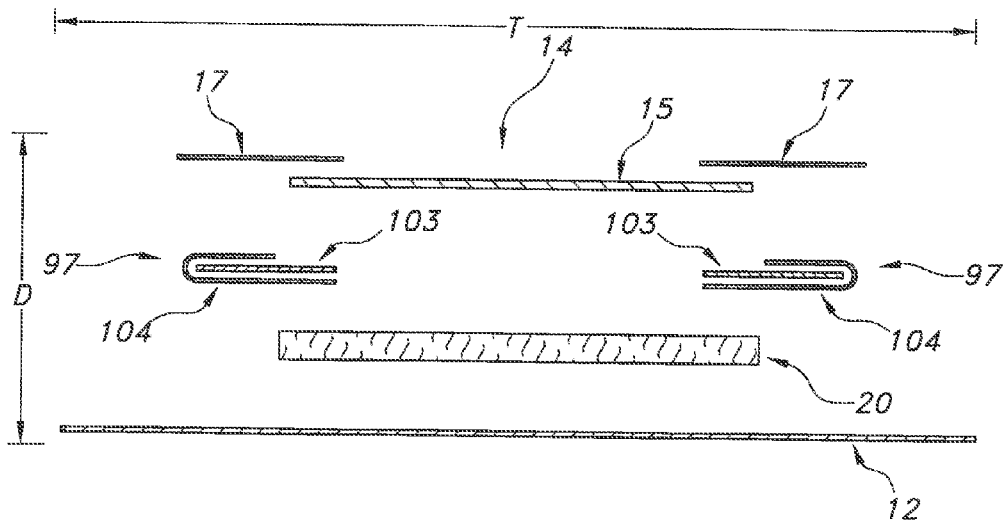
FIG. 1I is an exploded cross-sectional view of an alternative embodiment of the feminine hygienic pad of FIG. 1 of the present invention, taken at approximately lines 1I-1I.

In still a further alternative embodiment, as shown in exploded cross sectional view in FIG. 1I, decolorizing structures 97 include a hydrophilic nonwoven layer 103 which is partially wrapped by a hydrophobic barrier material 104 in order to separate any insults in the absorbent core layer 20 from the decolorizing structures 97.

Figure 1J:
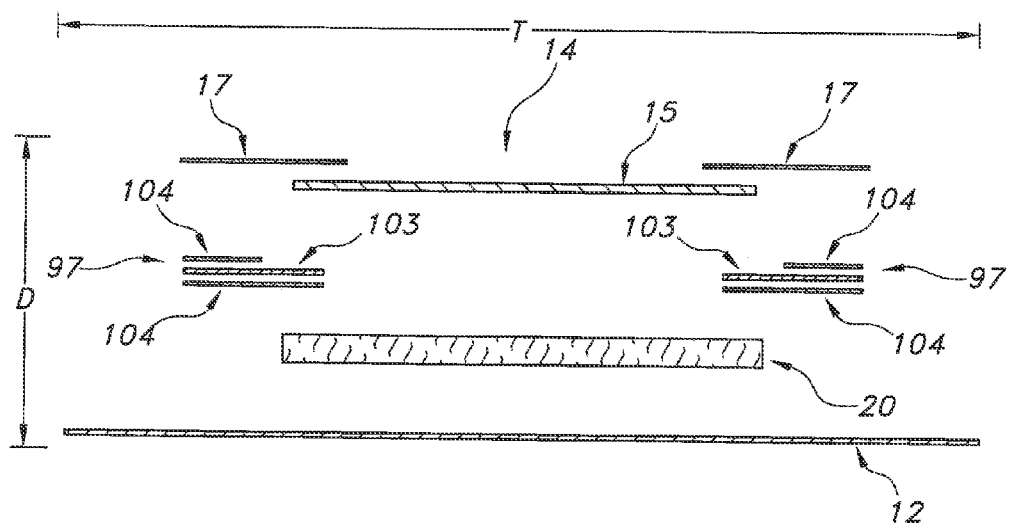
FIG. 1J is an exploded cross-sectional view of an alternative embodiment of the feminine hygienic pad of FIG. 1 of the present invention, taken at approximately lines 1J-1J.
Figure 1K:
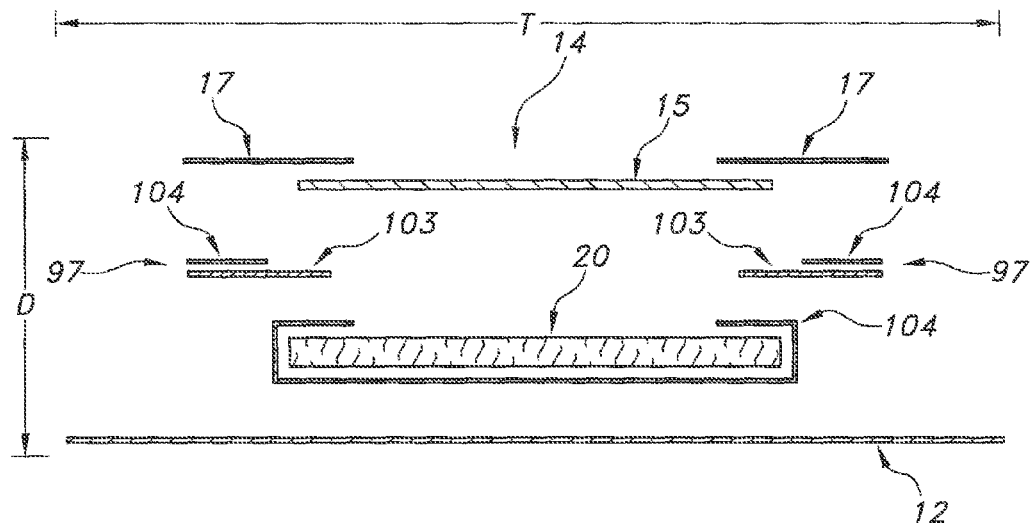
FIG. 1K is an exploded cross-sectional view of an alternative embodiment of the feminine hygienic pad of FIG. 1 of the present invention, taken at approximately lines 1K-1K.
Figure 1L:
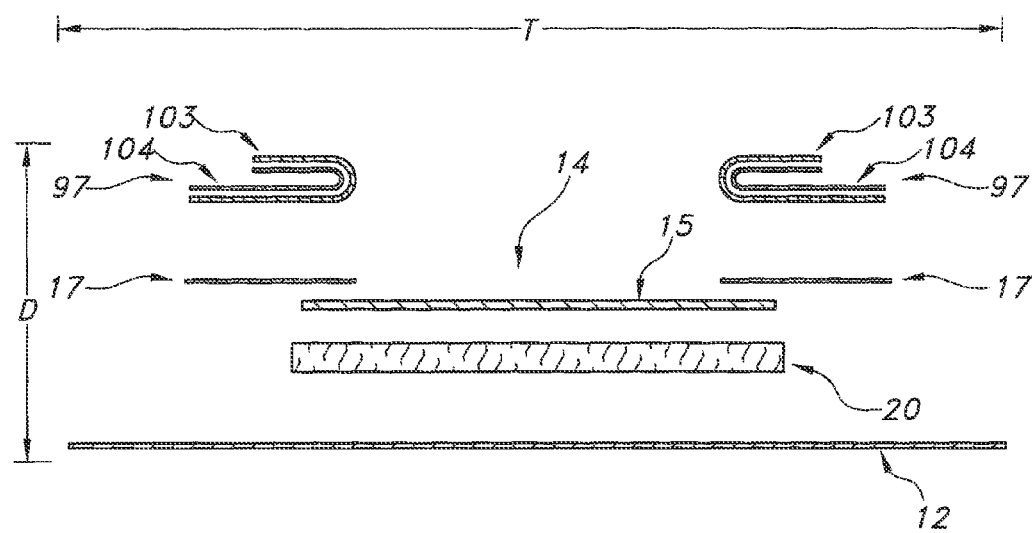
FIG. 1L is an exploded cross-sectional view of an alternative embodiment of the feminine hygienic pad of FIG. 1 of the present invention, taken at approximately lines 1L-1L.

In yet a further alternative embodiment, as shown in exploded cross sectional view in FIG. 1J, decolorizing structures 97 include a hydrophilic nonwoven layer 103 which is partially covered by hydrophobic barrier materials 104 in order to separate any insults in the absorbent core layer 20 from the decolorizing structures 97. The hydrophobic barrier material 104 partially covers one side of the hydrophilic nonwoven layer 103, and completely covers the other side of the nonwoven layer facing the absorbent core layer. In still a further alternative embodiment as shown in exploded cross-sectional view in FIG. 1K, the hydrophilic nonwoven layers 103 of the decolorizing structures 97 are partially covered by a hydrophobic barrier material 104, and the absorbent core layer 20 is partially enclosed by a hydrophobic barrier material 104 so as to prevent contact of insult in the absorbent core layer 20, with the hydrophilic nonwoven layer 103, In still another alternative embodiment, as shown in exploded cross-sectional view in FIG. 1L, decolorizing structures 97 in the form of folded "U" shaped laminates of layers 103, 104 are positioned on top of the topsheet layer 14 adjacent the pad/article lateral side edges, Finally, it should be recognized that each of the described decolorizing structures may, in alternative embodiments, be used in conjunction with decolorizing chemical agents, which through chemical reaction or other binding mechanism cause the filtering or agglomeration of the coloring agents of menses within the structures, or elsewhere in the article.

By employing the decolorizing structures described herein, a targeted decolorizing region is created at, along, partially adjacent, or adjacent the pad's lateral side edges. In this manner, the decolorizing structure helps to discharge color from potentially stain-producing exudates at the edges of the pad product, and desirably off of the topsheet layer, where leakage is most likely to occur in modern feminine hygiene absorbent personal care articles. Interior regions of the product may be left substantially unhindered by the decolorizing structures, thereby allowing the decolorizing structures to target menses at specific peripheral locations. This enables a user to observe and inspect the bodily exudates in the center (central insult receiving region/portion) of the product, and also allows the deodorizing structures to be applied only to those portions of the product needed to achieve the desired effect so that the untreated regions can continue to fulfill their functions, such as absorbing or wicking fluids, etc. without undue stiffness or sacrifice in comfort. In addition, the use of targeted decolorizing structures in conjunction with masking elements (if desired) provides additional emotional comfort to users who prefer not to view the spread of menses insult stains from the topsheet user-facing surface, and while also seeking comfort in knowing that leakage that may result from such pad will result in less visibly apparent staining on a garment or bedding.

Figure 2A:
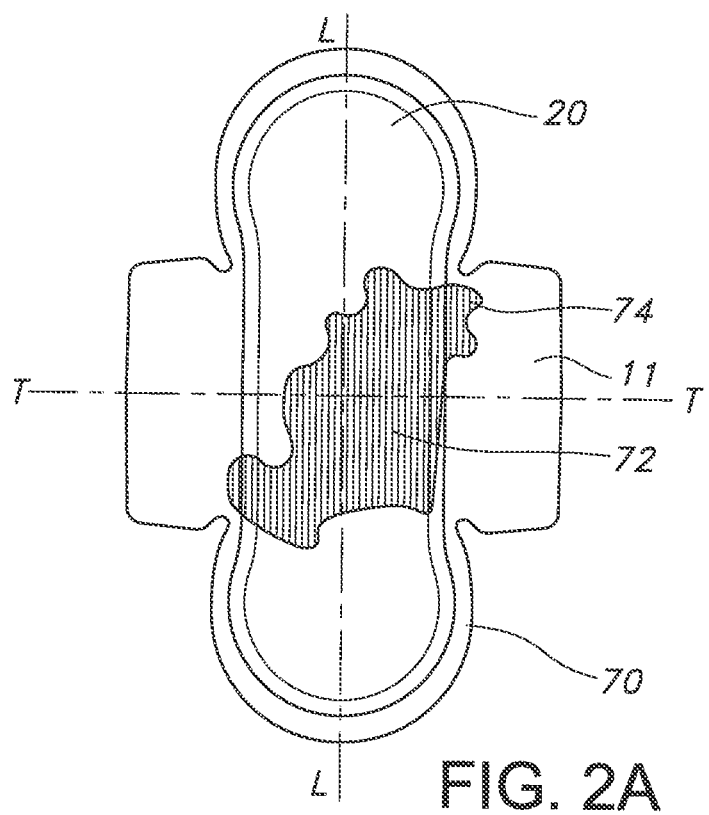
FIG. 2A is a stylized view of a prior art feminine hygienic pad including traditional menses insult soiling.
Figure 2B:
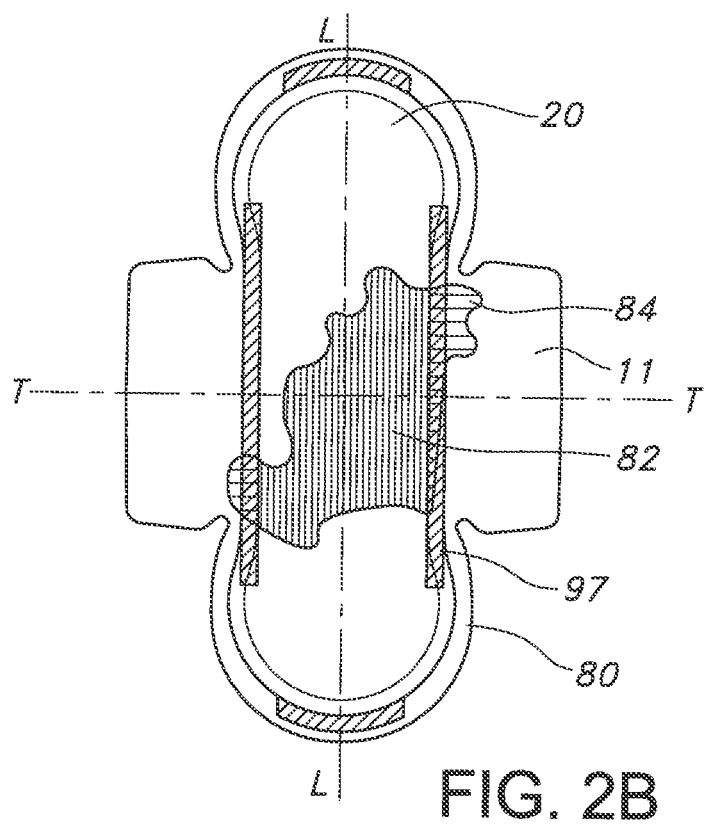
FIG. 2B is a stylized view of a feminine hygienic pad of the invention illustrating menses insult soiling and targeted stain altering, in accordance with a decolorizing structure embodiment of the invention.

As can be seen in FIG. 2A, which illustrates the progression of a menses insult stain in certain traditional feminine hygienic pads, the menses stain 72 may move on the topsheet layer, internal pad layer or absorbent core layer towards the wings 11 of a pad 70. As the stain spreads, it retains its red color towards the wings 11, as seen on the wings 74. In comparison, an insult stain of a pad of the invention 80 as seen in FIG. 2B, demonstrates a certain initial color stain on the topsheet layer, internal pad layer or absorbent core layer 82. As the pad structure changes towards the lateral edges, the insult stain 84 and spreading menses experience a color change from the initial stain 82, as the menses exudates progress towards the wings 11 through and/or across the decolorizing structure 97. Additionally, the stain along these areas may be masked as well.

It has been found that fibrous layer substrates, such as the nonwoven strip materials described, with a particular pore gradient/ratio in the D-axis, and strategically placed at targeted areas within an absorbent article, provide color filtration for menses exudates. In particular, it has been found that nonwoven laminates with decreasing pore sizes in the laminate along the D-axis, and in particular having an average pore size ratio of between 1:1 and 1:0.01 between a first nonwoven material and a second nonwoven material, placed at positions adjacent to pad product side edges, reduces (and masks) stain color towards a product side edges. It is observed that two factors of the base nonwoven substrate contribute to the filtration effect, the first being the pore size of the nonwoven substrate, and the second being the wicking capability of the nonwoven substrate. It further has been found, that laminates of fibrous substrates and hydrophobic barriers (either in the form of nonwoven layers and/or film sheets) also can serve as menses colorant filters and masking elements, when formed into particular structures and placed in targeted areas within a feminine hygiene absorbent personal care article. By using filtering and masking decolorizing structures along absorbent article lateral side edges, the color of a menses stain can be reduced.

It has been found that feminine pad leakage often results from residual pad menses insults on or near the topsheet layer, user-facing surface of a pad. Such residual insult either is not contained by the absorbent layer(s) as a result of fluid saturation of the layer or impeded flow of an insult into the absorbent structure. By "impeded", it is meant that such flow is either slowed or restricted as a result of the absorbent layer structure, or alternatively, not absorbed quickly enough as a result of a sudden insult. Such impeded flow can result in run-off of insult from the pad, even when the absorbent layer is not saturated. With the development of, and popularity of progressively thinner and smaller (surface area) feminine care pads and liners, the potential for leakage has been amplified. Depending on design features, such pads may have less overall capacity, having smaller absorbent areas. When an absorbent layer is saturated, the menses insult can pool on the surface of the pad which can subsequently run off the side edges of the pad to a garment or bedding, or be transferred via body contact to a garment or bedding. As runoff and pooling are often the immediate causes of staining in thinner feminine pads, the described invention has addressed such causes by directing fluid flow not only in absorbent layers, but also in non-absorbent layers at side edges of a pad. Further, the described invention has assisted in reducing overall topsheet layer stain size as a result of both decolorizing structures on layers and the use of stain masking technology in conjunction with such decolorizing structures. Such reduction in stain size has led to smaller topsheet layer stain sizes, and relatively larger, interiorly-situated or absorbent core layer stain sizes (overall stain size surface area) when compared to the topsheet layer stain size. Such reduced color (in lateral pad areas) and reduced stain size, can help provide comfort, and instill confidence to some consumers who wear such absorbent products. Finally, by separating color producing components of menses within the feminine hygienic pad, by use of strategically placed and constructed decolorizing structures, lower viscosity components of menses may be absorbed more efficiently by the absorbent core layer structures.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalent thereto.

I claim:

1. A feminine hygiene absorbent personal care article having lateral side edges, comprising a topsheet layer, a backsheet layer, an optional additional pad interior layer, and at least one absorbent core layer having lateral side edges, said at least one absorbent core layer positioned between said topsheet layer and said backsheet layer, said feminine hygiene absorbent personal care article further having a longitudinal axis, a transverse axis, and a depth axis, wherein at least one decolorizing structure is positioned on at least one of the topsheet layer, the at least one absorbent core layer, the backsheet layer, optional additional pad interior layer or between one or more of the above layers, said decolorizing structure being adjacent said article lateral side edges, which decolorizing structure extends laterally beyond the lateral side edge of the absorbent core layer along said transverse axis, wherein said decolorizing structure is a laminate of two nonwoven materials, and further, wherein said two nonwoven materials comprise a first nonwoven material having an average pore size of between about 50 and 200 microns, and a second nonwoven material having an average pore size of between about 3 and 40 microns.

2. The feminine hygiene absorbent personal care article of claim 1, wherein said decolorizing structure is positioned on said topsheet layer.

3. The feminine hygiene absorbent personal care article of claim 2, wherein said topsheet layer includes a central longitudinally directed topsheet material and two longitudinally directed side edge topsheet materials, and further wherein said decolorizing structure is positioned on said two longitudinally directed side edge topsheet materials.

4. The feminine hygiene absorbent personal care article of claim 3, wherein said two longitudinally directed side edge topsheet materials are comprised of a laminate including a masking layer.

5. The feminine hygiene absorbent personal care article of claim 4, wherein said laminate of said two longitudinally directed side edge topsheet materials includes a nonwoven and film layer.

6. The feminine hygiene absorbent personal care article of claim 1, wherein said decolorizing structure laminate is placed on each longitudinally directed side edge of the article.

7. The feminine hygiene absorbent personal care article of claim 1, wherein said first nonwoven material having an average pore size of between about 50 and 200 microns, has a basis weight of between about 10 and 70 gsm, and said second nonwoven material having an average pore size of between about 3 and 40 microns, has a basis weight of between about 10 and 100 gsm.

8. The feminine hygiene absorbent personal care article of claim 1, wherein said first nonwoven material having an average pore size of between about 50 and 200 microns, has an average fiber diameter size of between about 2 and 20 microns, and said second nonwoven material having an average pore size of between about 3 and 40 microns, has an average fiber diameter size of between about 0.2 and 10 microns.

9. The feminine hygiene absorbent personal care article of claim 1, wherein said decolorizing structure laminate extends along the side edges on the topsheet layer or other layers, between about 30 and 99 percent of the length of the article.

10. The feminine hygiene absorbent personal care article of claim 1, wherein said decolorizing structure laminate extends along the entire length of the article.

11. The feminine hygiene absorbent personal care article of claim 1, wherein said decolorizing structure laminate includes a color different from that of the color of the layer underlying the decolorizing structure laminate.

12. A feminine hygiene absorbent personal care article having a front and back end, lateral side edges, and comprising a topsheet layer, a backsheet layer, an optional additional pad interior layer, and at least one absorbent core layer having lateral side edges, said at least one absorbent core layer positioned between said topsheet layer and said backsheet layer, said feminine hygiene absorbent personal care article further having a longitudinal axis, a transverse axis, and a depth axis, wherein at least one decolorizing structure is positioned on at least one of the topsheet layer, the at least one absorbent core layer, the backsheet layer, optional additional pad interior layer or between one or more of the above layers, said decolorizing structure being adjacent said article lateral side edges, which decolorizing structure extends laterally beyond the lateral side edge of the absorbent core layer along said transverse axis, and further, wherein additional decolorizing structures are placed on the front and back ends of the article.

\* \* \* \* \*